(12) United States Patent  
Novak

(10) Patent No.: US 8,884,769 B2  
(45) Date of Patent: Nov. 11, 2014

(54) DIMENSIONALLY-SENSITIVE MOISTURE SENSOR AND AN ALARM SYSTEM FOR AN ABSORBENT ARTICLE

(76) Inventor: Guy R. Novak, San Diego, CA (US)

( * ) Notice: Subject to any disclaimer, the term of this patent is extended or adjusted under 35 U.S.C. 154(b) by 286 days.

(21) Appl. No.: 13/439,853

(22) Filed: Apr. 5, 2012

(65) Prior Publication Data

US 2012/0256750 A1  Oct. 11, 2012

Related U.S. Application Data

(60) Provisional application No. 61/471,701, filed on Apr. 5, 2011.

(51) Int. Cl.
 *G08B 23/00* (2006.01)
 *A61F 13/42* (2006.01)
(52) U.S. Cl.
 CPC ...................................... *A61F 13/42* (2013.01)
 USPC ...................... 340/573.5; 340/573.1; 340/540
(58) Field of Classification Search
 USPC .................................... 340/573.1, 573.5, 540
 See application file for complete search history.

(56) References Cited

U.S. PATENT DOCUMENTS

| | | | |
|---|---|---|---|
| 4,246,575 A | 1/1981 | Purtell et al. | |
| 4,356,818 A | 11/1982 | Macias et al. | |
| 5,266,928 A | 11/1993 | Johnson | |
| 5,463,377 A | 10/1995 | Kronberg | |
| 5,469,146 A | 11/1995 | Gurler | |
| 5,709,222 A | 1/1998 | Davallou | |
| 5,797,892 A * | 8/1998 | Glaug et al. | 604/361 |
| 6,160,198 A | 12/2000 | Roe et al. | |
| 6,395,955 B1 | 5/2002 | Roe et al. | |
| 6,580,013 B1 | 6/2003 | Belloso | |
| 6,583,722 B2 | 6/2003 | Jeutter et al. | |
| 7,221,279 B2 | 5/2007 | Nielsen | |
| 7,498,478 B2 | 3/2009 | Long et al. | |
| 8,053,625 B2 | 11/2011 | Nhan et al. | |
| 2004/0113801 A1* | 6/2004 | Gustafson et al. | 340/604 |
| 2007/0260209 A1 | 11/2007 | Brillman | |
| 2008/0074274 A1 | 3/2008 | Hu et al. | |
| 2009/0149825 A1* | 6/2009 | Berland et al. | 604/361 |
| 2009/0174559 A1* | 7/2009 | Rondoni et al. | 340/573.5 |

* cited by examiner

Primary Examiner — Travis Hunnings

(57) ABSTRACT

An apparatus and method for detecting moisture in a diaper is disclosed. A moisture sensor apparatus is comprised of a housing made of material dimensionally-sensitive to moisture, such that the housing will expand or contract. Electrically conductive contacts disposed on/in the housing, are selectively coupled to, or decoupled from, each other based on a dimensional change of the sensor device when it comes into contact with moisture. An electrical signal routable through the electrically conductive contacts detects a change in state, e.g., from open to closed, and activates a local or remote alarm to indicate the presence of moisture. The consumable low-cost sensor and the optional non-metallic leads and contacts, that are at least partially biodegradable, are coupled via a convenient slidable brush connector to a resusable alarm system having optional low duty cycle transmitting capability to a receiver base station, thereby providing a cost-effective, eco-friendly and user-friendly system.

20 Claims, 20 Drawing Sheets

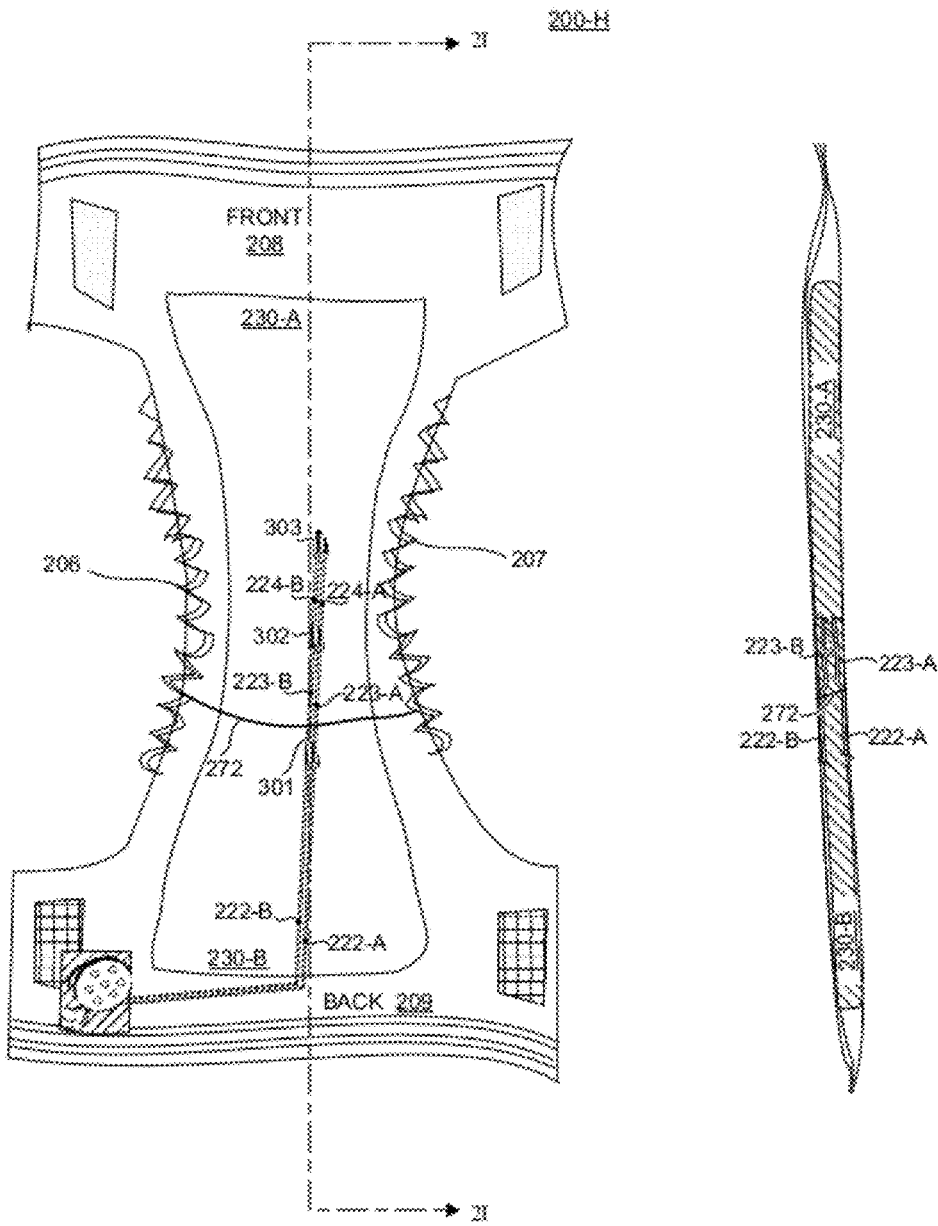
FIGURE 2H          FIGURE 2I

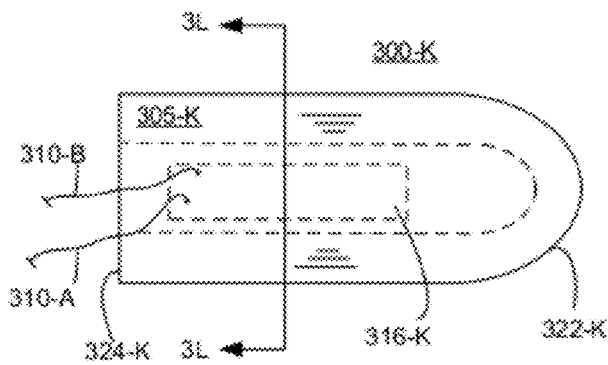
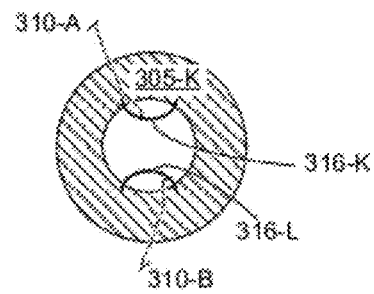
FIGURE 3K  FIGURE 3L
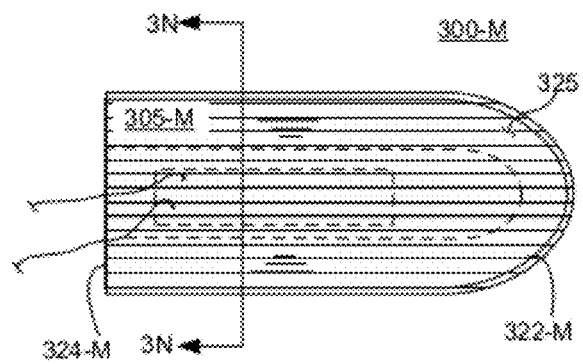
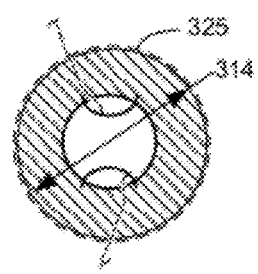
FIGURE 3M  FIGURE 3N
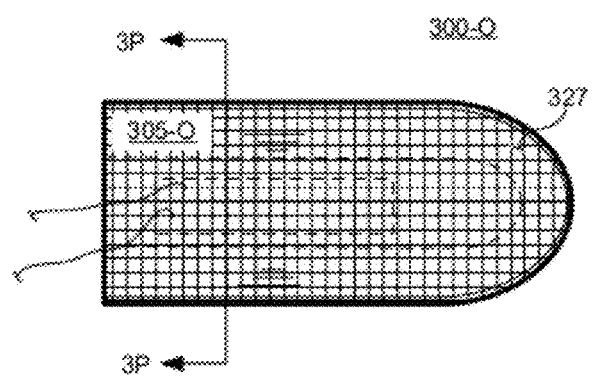
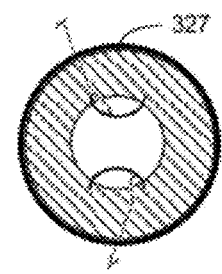
FIGURE 3O  FIGURE 3P

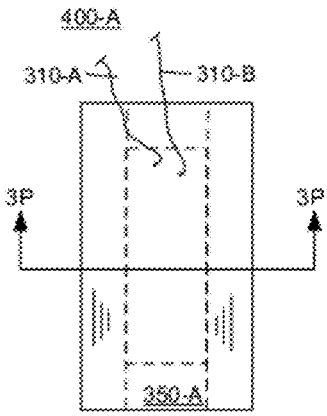
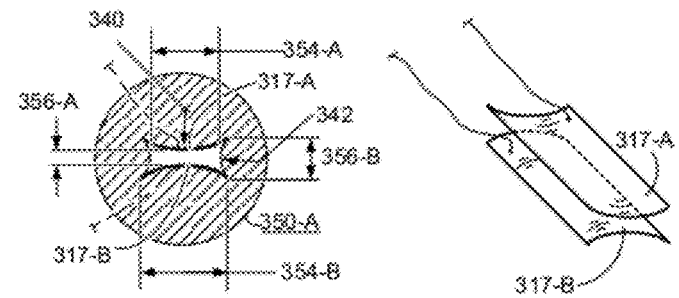
FIGURE 4A
FIGURE 4B FIGURE 4C
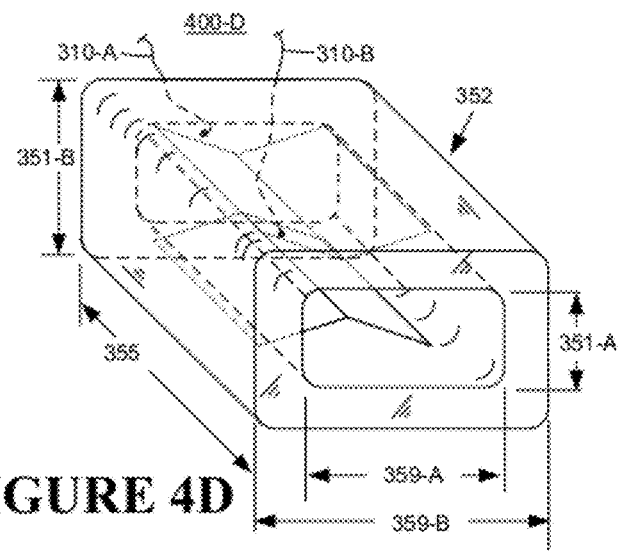
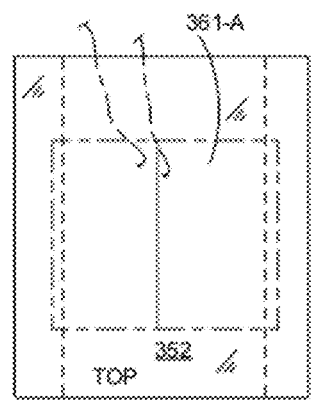
FIGURE 4D FIGURE 4E
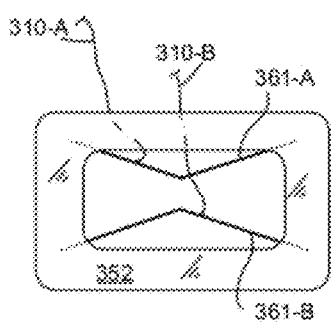
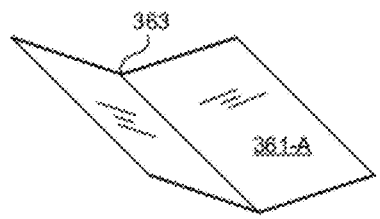
FIGURE 4F FIGURE 4G

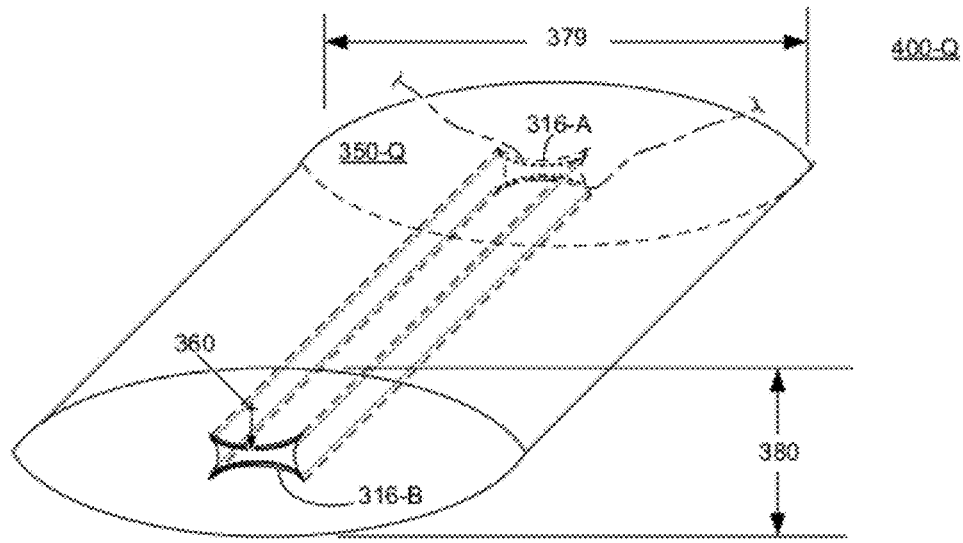
FIGURE 4Q
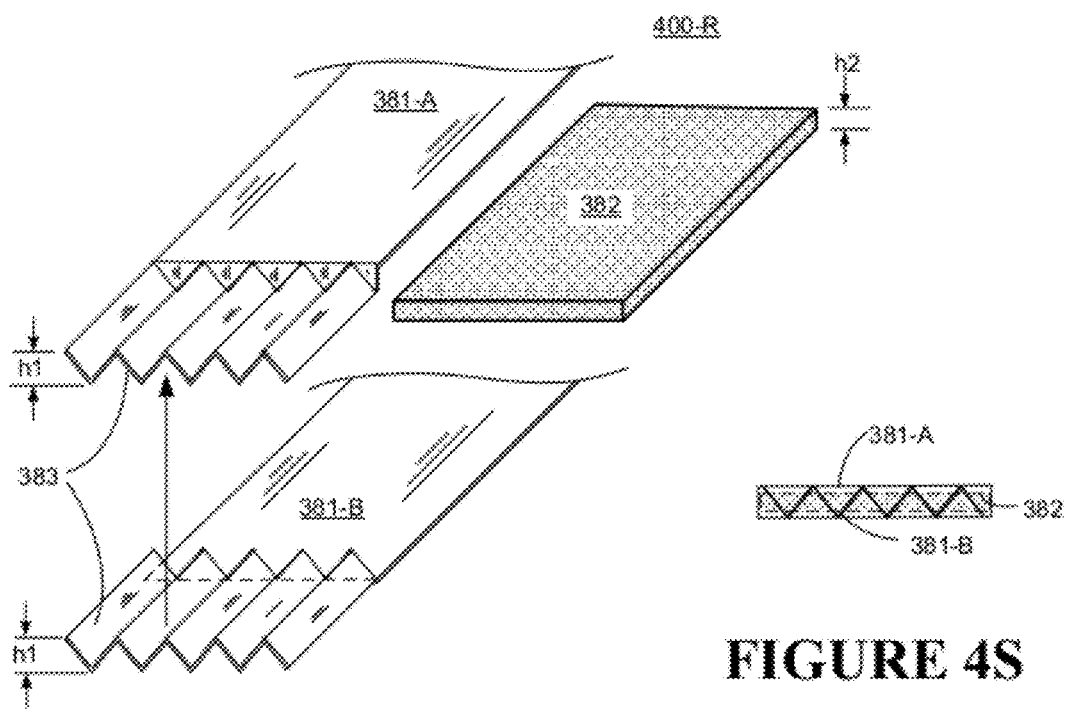
FIGURE 4R
FIGURE 4S

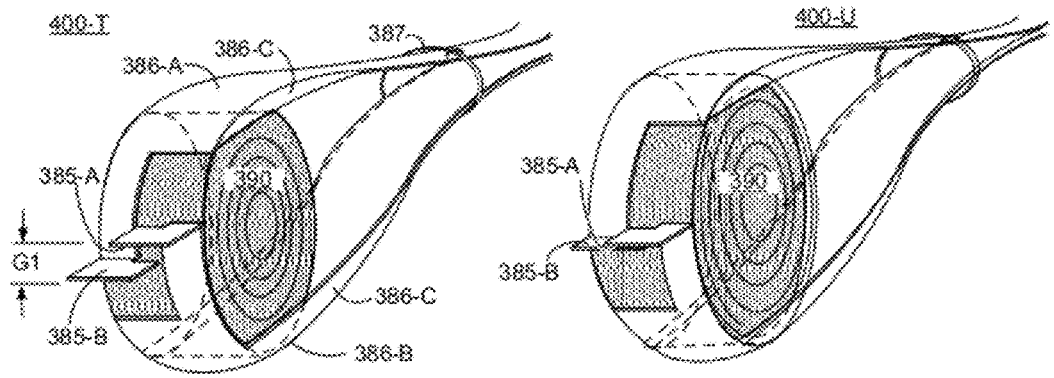
FIGURE 4T  FIGURE 4U
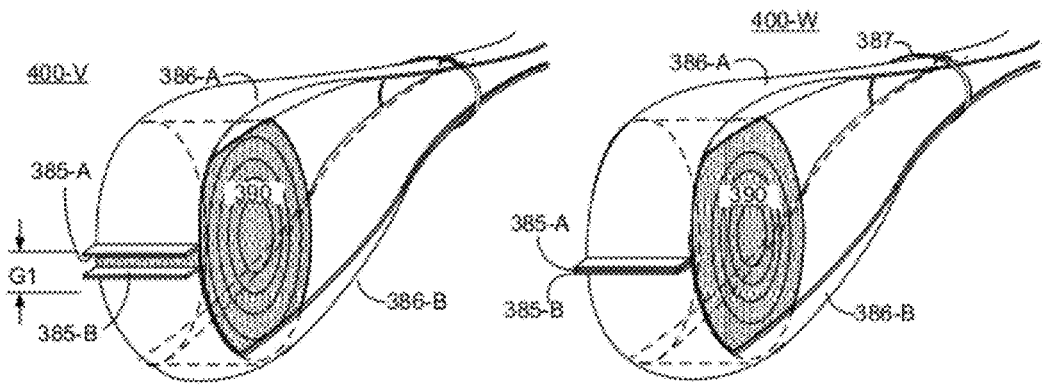
FIGURE 4V  FIGURE 4W
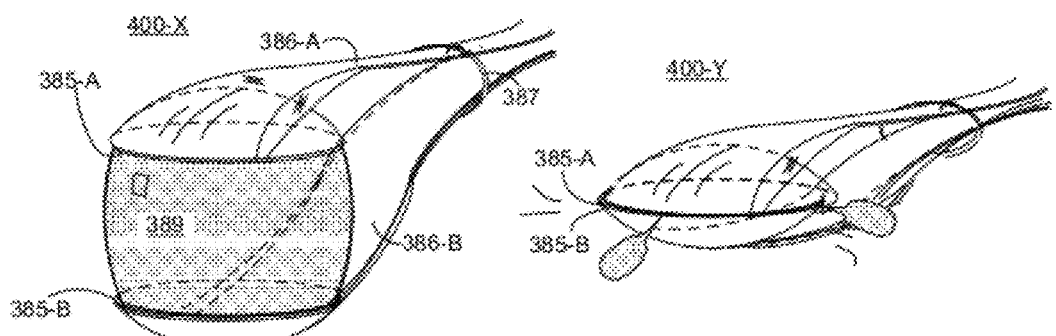
FIGURE 4X  FIGURE 4Y

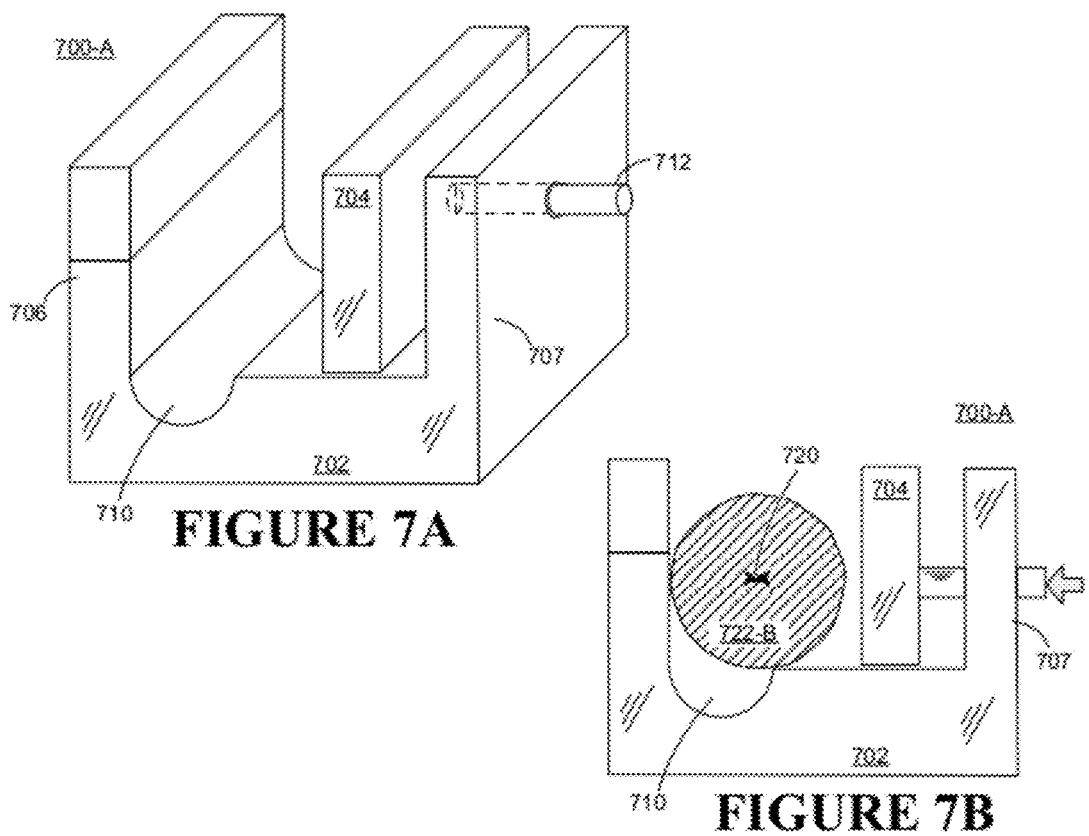
FIGURE 7A
FIGURE 7B
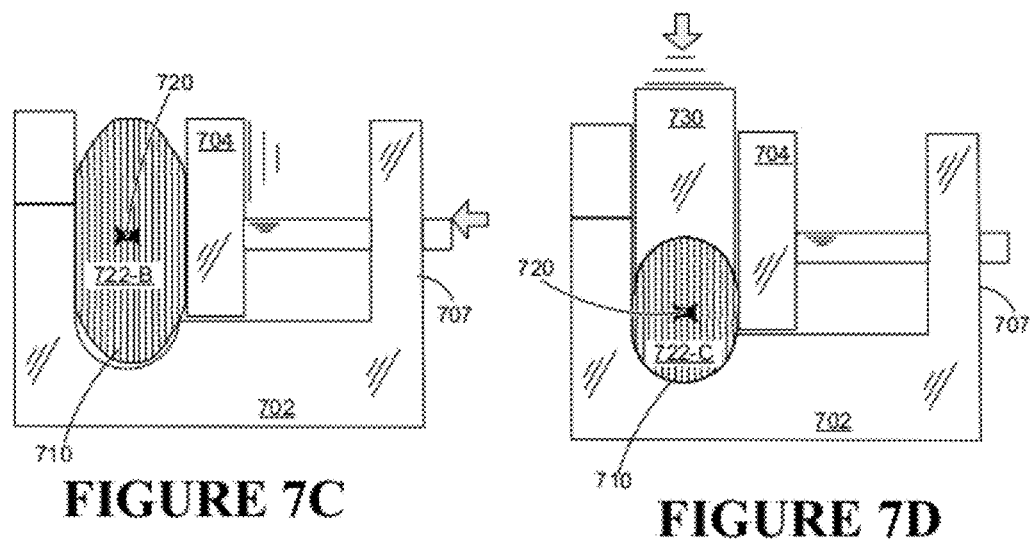
FIGURE 7C
FIGURE 7D

DIMENSIONALLY-SENSITIVE MOISTURE SENSOR AND AN ALARM SYSTEM FOR AN ABSORBENT ARTICLE

REFERENCE TO RELATED APPLICATIONS

This application claims priority to provisional application, U.S. Ser. No. 61/471,701 filed Apr. 5, 2011, entitled MOISTURE DETECTION SYSTEM FOR DIAPERS, which application is also incorporated herein by its reference, in its entirety.

DESCRIPTION OF THE RELATED ART

Disposable absorbent articles such as diapers and adult incontinence briefs are useful to prevent body exudates, such as urine, feces, menses, etc., also known as insult, from soiling, wetting, or otherwise contaminating clothing or other articles, such as bedding, that may come in contact with the wearer. However, any exposure of skin over an extended period of time following the release of bodily exudates increases the difficulty of cleaning and increases the likelihood of chronic residual contamination, in addition to rashes and sores on the wearer. The undesirable effects of leakage and/or improper containment, difficult cleanup, and/or residual skin contamination are especially evident with regard to fecal matter captured in the diaper. Feces remaining in the diaper for an extended period of time can harm the skin of the wearer over time and feces leaking from the diaper almost always results in an unpleasant and messy clean-ups. Regardless of the attempts to add features to diapers, such as pockets, spacers, apertured top sheets, and the like, to limit the movement of the fecal material across the top sheet and/or to better confine the fecal matter in the diaper, timeliness of changing the diaper once bodily exudates have been deposited is of the most significant factors in preventing sores and rashes.

SUMMARY

An apparatus, system, and method of manufacture of a moisture detection system are disclosed. The moisture detection system includes: a moisture-resistant layer; an absorbent material disposed on the moisture-resistant layer; one or more dimensionally-sensitive, or dimensionally-changing, sensors, or moisture sensors, for detecting the presence of moisture, disposed in or on the absorbent material; a plurality of electrically conductive leads, wherein each of the electrically conductive leads is respectively coupled to one of the plurality of electrically conductive contacts on the moisture sensor; an alarm system coupled to the moisture sensor, wherein the alarm system is activated by a change in the state of the electrical contacts in the sensor device, thereby drawing attention to a change in status of the absorbent material. The moisture sensor has a plurality of electrical contacts coupled thereto, and the moisture sensor detects moisture in the absorbent article by changing a state of the electrical contacts from a normally open position to a closed position, or from a normally closed position to an open position, under a force of mechanical expansion or contraction of the sensor in the presence of moisture.

A single alarm system can be coupled to multiple or all sensors to provide an alarm signal should any one of the moisture sensors undergo a change in state. Alternatively, unique alarm indicators can be coupled independently to one or more of the plurality of sensors, in one or more different locations and thereby provide a unique alarm indication, e.g., audio, tactile, visual, data, wireless signal, etc., to indicate a specific location in the diaper that has moisture, or to indicate a specific type of fluid or discharge typical of the location of the sensor, or the moisture content of the discharge. The material used for a housing of the moisture sensor can be more sensitive to a specific type of moisture, for a designated position in a diaper, and thus would be biased to create a change in state to activate the alarm when the specific type of moisture is present, e.g., urine vs. feces. An optional wireless transmitter, coupled by a conductor to the alarm and sensor and wirelessly coupled to a base unit, can provide remote notification of an alarm triggered in a diaper. An optional operational indicator coupled to the alarm device can indicate the operational status of the transmitter and/or the operational status of the battery source, e.g., charged vs. discharged, for improved reliability. In different embodiments, the electrical contacts and/or the electrically conductive leads are made from: an electrically conductive polymer, that is at least partially biodegradable or is fully biodegradable, e.g., made of carbon black, or is non-biodegradable, e.g., metallic. Conductivity can be enhanced by doping electrical contacts/conductive leads with a performance-enhancing conductor, such as nickel, silver, etc. or by using a carbon nanotube conductive "wire" made from sheets of graphene.

The alarm system, with the alarm indicator, operational indicator, transmitter, and an optional receiver base station, is selectively removable from the absorbent article system having a moisture indicator. Thus the alarm system, as the most costly portion of the absorbent system, can be reused on subsequent absorbent articles with a moisture sensor, e.g., diapers, by selectively removing the alarm system and inserting it into a fresh absorbent article. As a result, this system design architecture allows for ultra-low production cost due to throw-away low-cost disposable sensor(s) and the reuse of high-cost electronics. Specifically, an ultra low cost diaper moisture detection system is produceable for pennies per diaper in terms of both the disposable portion and the resusable portion of the system. For example, the cost of the disposable portion is nominally $0.01/diaper or less, including the cost of sensor, lead, and contact, while the cost of the reusable portion is similarly $0.01/diaper or less, when averaging the higher cost of electronics across, perhaps a hundred or more diaper changes.

In another embodiment, a diaper has a moisture resistant barrier, between a first absorbent pad disposed towards the front portion of the diaper for absorbing urine, and a second absorbent pad disposed towards the back of the diaper for containing or absorbing feces, thereby preventing urine from triggering a moisture sensor disposed in the second absorbent pad, and preventing feces from triggering a moisture sensor disposed in the first absorbent pad. The first and second absorbent pad can be the same contiguous pad, separated by the barrier that resists or prevents communication of moisture, or they can be physically separate joined together via a barrier. An optional single baffle barriers or a plurality of baffle barriers coupled transversely across a crotch portion of the diaper between a first leg opening to a second leg opening, wherein the baffle sheet has a top uncoupled edge having an optional elastic member therein; and an optional centerline sheet traveling longitudinally from the front of the diaper to the back of the diaper and located in between the two leg openings in order to coincide with the location between the left and right gluteus maximus.

A moisture sensor for detecting moisture in a diaper is also disclosed. In particular, the sensor, or moisture sensor, device is comprised of a housing made of material that is electrically insulative and dimensionally-sensitive, or dimensionally-reactive, to the presence of moisture, e.g., the housing will expand or contract in the presence of moisture but is dimensionally stable when dry. Dimensionally stable means the size and shape of the housing are substantially unchanged. That is, when the housing is in an essentially moisture free environment, e.g., without any liquid discharge from the user, then the housing and the contacts remain in their normal state, e.g., normally open or normally closed. Thus, the material for the housing would be dimensionally stable in a nominal environment with body perspiration and humid ambient environments.

The housing of the moisture sensor has an outer surface and an optional cavity formed therein. A plurality of electrically conductive contacts, disposed on or in the housing, e.g., any combination of surfaces such as the outer surface and/or on an inner surface of a cavity in the housing, are selectively moved to make contact with each other as a result of a dimensional change of the housing arising from a change from a dry state to a moist or wet state when the sensor device comes into contact with moisture. That is, the contacts in the sensor are selectively coupled to make or break contact depending upon the moisture levels. An electrical signal routable through the plurality of electrically conductive contacts will monitor a switching condition, e.g., opening or closing of the electrically conductive contact circuit, that activates a local or remote alarm to indicate the presence of moisture. The plurality of electrically conductive contacts can either be initially disposed apart from each other in a substantially dry environment to represent a normally open circuit, or can be initially disposed against each other in a substantially dry environment to represent a normally closed circuit. Thus the moisture sensor detects moisture in a diaper by changing the state of electrical contacts under the force and displacement from mechanical expansion or contraction of the sensor device in the presence of moisture. The housing uses highly compressed moisture-absorbing material that is formed into a shape having a cylindrical, oval, or rectangular cross-section though any shape that enables a dimensional change is contemplated by the present disclosure. In one embodiment, a portion of the sensor device is biodegradable, e.g. the sensor housing. In another embodiment, the entire sensor device is biodegradable, e.g., the sensor housing, and leads and contacts electrical components are biodegradable.

Material used for the sensor housing can be: cotton, viscous rayon, hydrophilic biodegradable polyester, polymer fibers such as polylactic acid, segmented linear polyurethanes, segmented cross linked polyurethanes, or any other material that has dimensional stability in a dry state and expands or contracts in a moist or wet state such that it could trigger a change in a circuit, or any combination of these materials. Additionally, the housing has a stiffness that substantially maintains the cavity formed therein in order to maintain an open circuit without the contacts touching in a dry environment. The sensor device is a consumable one-time use device in one embodiment. In the presence of moisture, the housing can expand and the cavity formed therein can collapse or constrict in order to close or open contacts, depending upon the circuit design, to thereby provide a change in an electrical signal to indicate the existence of the moist or wet environment. In particular, the dimensional change to the housing of the sensor device can be one or more dimensions, e.g., it can expand linearly only, can expand linearly and radially, can expand radially but not linearly, or can expand in 2-3 axes, e.g., all dimensions. The weave design of the moisture expanding material can have a directional preference, e.g., fiber or cell orientation, to moisture absorbance, and thus dimensional change. The sensor device includes an optional outer layer disposed around the housing, wherein the outer layer helps to maintain the shape, or outer surface, of the housing, in one embodiment. The outside layer is a fibrous material disposed on the outer surface of the moisture-expanding material in order to inhibit expansion of the outer surface of the moisture-expanding material and to promote closure of the cavity formed inside the housing. The fibrous material is a mesh, a net, or a winding of organic or inorganic material that conducts moisture to the sensor housing.

A method of fabricating a diaper with the moisture detection and alarm is also disclosed. The method comprises one or more processes of: creating a moisture-proof backing layer; disposing a portion of a moisture absorbent padding on the moisture-proof backing layer; disposing at least one sensor device on or in the moisture-absorbent padding, wherein the sensor device is for detecting moisture in a diaper, and is made of material dimensionally-sensitive to the presence of moisture; coupling the sensor with a first and second electrically conductive lead, e.g., a conductive wire or strip, wherein the first and second electrically conductive leads are separated by electrically insulative layers of the diaper; and disposing the electrically conductive wire or metal strip on the moisture-proof backing layer, on or in the moisture absorbent padding, and/or an electrically insulative layer of the diaper, including optional retention means of adhesive, stitching in the pad, or forming therein.

The methods, systems, and apparatuses disclosed herein may be implemented in any means for achieving various aspects of the present disclosure. Other features will be apparent from the accompanying drawings and from the detailed description that follows.

BRIEF DESCRIPTION OF THE DRAWINGS

The drawings included herewith are incorporated in and form a part of this specification. The drawings illustrate one embodiment of the present disclosure and, together with the description, serve to explain the principles of the invention. It should be understood that drawings referred to in this description are not drawn to scale unless specifically noted.

FIGS. 2H and 2I are a top and section view, respectively, of a diaper laid flat with a moisture detection system having a plurality of moisture sensors on either side of a transverse moisture separator, according to one or more embodiments.

FIGS. 3K-3L are a top and cross-section view, respectively, of a moisture sensor with a round cross-section, and one closed end with no outer casing, according to one or more embodiments.

FIGS. 3M-3N are a top and cross-section view, respectively, of a moisture sensor with a round cross-section, one closed end and one open end, with a mesh casing around the outside, according to one or more embodiments.

FIGS. 3O-3P are a top and cross-section view, respectively, of a moisture sensor with a round cross-section, one closed end and one open end, with a continuous casing around the outside, according to one or more embodiments.

FIGS. 4A-4B are a top and cross-section view, respectively, of a moisture sensor with a round cross-section, open ends, with a two-axis hourglass-shaped cavity, according to one or more embodiments.

FIG. 4C is an isometric view of the contacts to be mated to the two-axis hourglass-shaped cavity of the moisture sensor, according to one or more embodiments.

FIG. 4D is an oblique view of a moisture sensor with a rectangular cross-section, and open ends, according to one or more embodiments.

FIGS. 4E and 4F are a top and front view, respectively, of the moisture sensor with a rectangular cross-section, according to one or more embodiments.

FIG. 4G is an isometric view of a contact for being disposing in the moisture sensor housing, according to one or more embodiments.

FIG. 4Q is an oblique view of a moisture sensor with an oval or clamshell cross-section, according to one or more embodiments.

FIGS. 4R and 4S, are isometric views of a saw tooth plate moisture sensor, according to one or more embodiments.

FIG. 4T through 4Y, are oblique views of three different embodiments of clamshell moisture sensors, according to one or more embodiments.

FIGS. 7A-7D are isometric and front views, respectively, of a manufacturing system for fabricating a moisture sensor, according to one or more embodiments.

Other features of the present embodiments will be apparent from the accompanying drawings and from the detailed description that follows.

DETAILED DESCRIPTION OF THE INVENTION

Reference will now be made in detail to the preferred embodiments of the invention. Examples of the preferred embodiment are illustrated in the accompanying drawings. While the invention will be described in conjunction with the preferred embodiments, it is understood that the invention is not limited to these embodiments. Rather, the invention is intended to cover alternatives, modifications and equivalents, which may be included within the spirit and scope of the invention, as defined by the appended claims. Additionally, in the following detailed description of the present disclosure, numerous specific details are set forth in order to provide a thorough understanding of embodiments of the present invention. However, it will be apparent to one of ordinary skill in the art that the present invention may be practiced without these specific details. In other instances, well-known methods, procedures, components, and operations have not been described in detail so as not to unnecessarily obscure aspects of the present invention.

Figure 1:
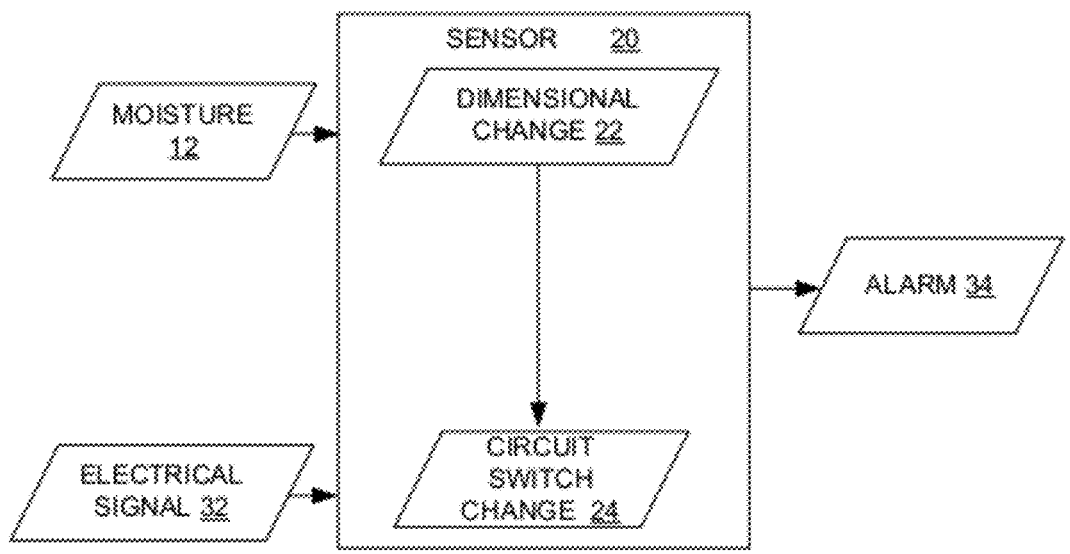
FIG. 1 is a block diagram of the functions performed by a dimensionally-changing moisture sensor, according to one or more embodiments.

Referring now to FIG. 1, a block diagram of the functions performed by a dimensionally-changing moisture sensor ("sensor") is shown, according to one or more embodiments. In particular, sensor 20 receives an input of moisture 12 that causes a dimensional change function 22 to a moisture sensor that subsequently causes a circuit switch change function 24.

An electrical signal input 32 to sensor function 20 will then be coupled via the circuit switch change function 24 to an alarm function 34. The functions herein can be accomplished by a wide range of apparatus and methods using a wide range of embodiments, some of which are provided herein for exemplary purposes, to achieve substantially the same results of moisture detection. For example, dimensional change function 22 can be accomplished by dimensional changes in any combination of directions using any type of coordinate system, e.g., radial, axial, width, height, inside diameter, outside diameter, etc. Circuit switch change function 24 can be implemented by any circuit that causes any kind of change in the circuit to activate alarm function 34.

Diaper Assembly with Moisture Sensor

Figure 2A:
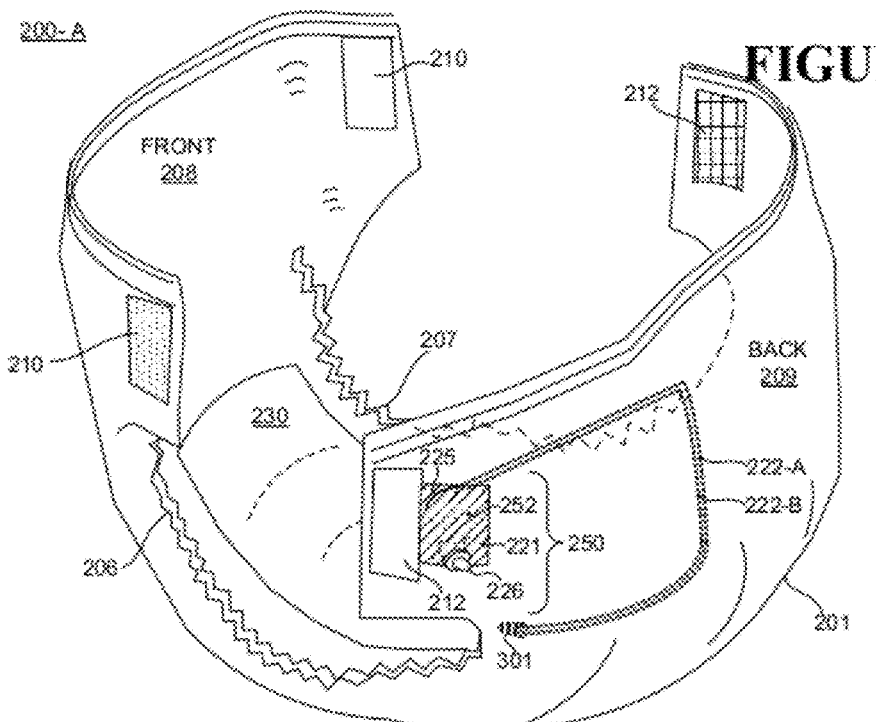
FIG. 2A is an isometric view of a diaper with a moisture detection system having a single moisture sensor, according to one or more embodiments.

Referring now to FIG. 2A, an isometric view of a diaper application of an absorbent article, with a moisture detection system having a single moisture sensor is shown, according to one or more embodiments. Diaper 200-A in the present embodiment is a layered construction of: a shell 201 which can be moisture resistant/proof; an absorbent material, or pad, 230 coupled to shell 201; a moisture sensor 301 disposed in or on absorbent pad 230, wherein moisture sensor 301 has a plurality of electrical contacts coupled thereto, shown in subsequent figures, and wherein moisture sensor 301 detects moisture in diaper 200-A by changing a state of the electrical contacts from a normally open position or a normally closed position to a closed or an open position, respectively, under a force of mechanical expansion or contraction of the sensor in the presence of moisture; a plurality of electrically conductive leads 222-A, 222-B wherein each of the electrically conductive leads is respectively coupled to one of the plurality of electrically conductive contacts in/on moisture sensor 301; an alarm system 250 coupled to the moisture sensor 301, wherein the alarm system 250 is activated by a change in the state of the electrical contacts in the sensor device 301, thereby drawing attention to a change in status of the 200-A. Absorbent articles include adult and infant diapers, training pants, bandages, etc., and any type of absorbent article where moisture detection is desired, whether in a biological or other application.

The benefit of a normally open circuit is that no electricity is flowing until the contact is closed, and at that time, the system is likely to be checked and replaced quickly, e.g., changing out a soiled diaper with a fresh one. Consequently, the user is only exposed to a minimal electrical or electromagnetic field. The alarm duty cycle of pulsing the sensor with a current signal, e.g., DC, to sense a change in state from a closed to open circuit, or from an open to closed circuit, can be any periodicity, e.g. once per every second or minute, or fractions or multiples thereof. Furthermore, the pulse can be any duration as to provide an accurate reading of the circuit, e.g., a fraction of a second. Thus, for example, a pulse sent every 1.0 second having a width of 0.01 seconds would result in a 1% duty cycle. The lower the duty cycle, the lower the exposure to electromagnetic fields, that in turn reduces any potential exposure to the user. While a low duty cycle substantially benefits a normally closed sensor that conducts current in the dry state, a duty cycle can also benefit a normally open switch after it has been activated and closed the circuit and is then conducting current. Any duty cycle to sense the alarm that yields reliable results is contemplated by the present disclosure. Alarm system 250 can use any type of alarm to provide notice of moisture in diaper 200-A such as one or more of: audio/tactile 252, wireless transmitter 225, visual 226, or any combination thereof. Pocket 221 houses alarm system 250 either permanently as an integrated part of diaper 200-A or as a flexible pocket, e.g., made of diaper material or other flexible material with elastic seams on a top edge or with hook and loop fastener to selectively retain alarm system 250. Wiring to alarm system 250 is permanently attached for a permanently sealed alarm system, or is selectively coupled to alarm system 250 for a transferrable alarm, allowing alarm system 250, a more expensive component, to be transferred from a soiled diaper to a fresh diaper for reuse.

Materials for diaper 200-A include: natural or organic fibers, manmade materials, or a combination thereof. Diaper 200-A can be either a disposable diaper or a reusable diaper. Specifically, a usable natural material for absorbent pad 230 include: industrial cotton, wool, bamboo, hemp or other organic material that absorbs moisture, or any combination thereof. Semi-synthetic and manmade materials for absorbent pad 230 include microfiber toweling, e.g., viscose rayon, super absorbent polymers (SAP) like sodium polyacrylate (SPA) polymers, or other manmade material that absorbs moisture. A stay-dry wicking top layer of absorbent pad 230 can be made of a material such as: polyester, fleece and faux suede to keep the layer against the user's skin as a non-absorbent layer, and thus reduce irritation. Shell 201 is impermeable in one embodiment and made of any type of waterproof material such as polyurethane laminate (PUL), etc., but can also be a moisture-resistant layer made of breathable polyethylene film or a nonwoven and film composite, or combination thereof.

Other typical structural features of diaper 200-A include: a front portion, or front face 208; a back face, or a back portion 209 each of which corresponds to a front portion of the wearer and the back portion of the wearer, respectively, as well as a leg openings 206 and 207 on the left and right side, respectively. Fastening tabs 210 couple to mating tabs 212, e.g., hook and loop fasteners, repositionable adhesive, refastenable tapes, snaps, safety pins, or any other type of fastener that allows retention of the front and back of the diaper to maintain the diaper in position, more or less, on the user. Diaper 200-A can be of the removable type with straps or as a 'pants' type diaper that fit over a cloth or disposable inset diaper, incontinence pads, e.g., adult diapers, etc.

Elastic leg openings 206, 207 of diaper 200-A provide sealing against legs of user, while providing flexibility for movement and normal body activities while wearing diaper. Front and back waistband 208 and 209 can have similar elastic sealing construction, with elastic or other memory type material that can be stretched and then return to approximately its original position and shape.

Electrically conductive leads 222-A, 222-B are electrically-conductive wires or strips that extend from the sensor device 301 and couple to an electrical circuit, e.g., alarm 250. The conductive leads 222-A, 222-B can have an electrically insulating layer around them, e.g., plastic, or can have no insulating layer on the wire or lead itself but rely instead on being insulated from each other in the diaper by separating leads 222-A and -B with electrically insulative diaper components, e.g., shell 201, or layer of absorbent pad 230. In one embodiment, the electrical contacts and/or the electrically conductive leads 222-A, 222-B are made from typical conductors such as copper or aluminum, while in another embodiment, they are made from electrically conductive polymer, that may or may not be biodegradable, such as composites including, but not limited to: polypyrrole (PPy) doped with butane sulfonic acid; and PPy doped with polystyrenesulfonate. Conductive ink deposited on a single side or both sides of a polymer substrate can also be used as a lead, as described hereinafter. However, any electrically conductive material may be used for the electrically conductive leads, wires, or contacts.

Figure 2B:
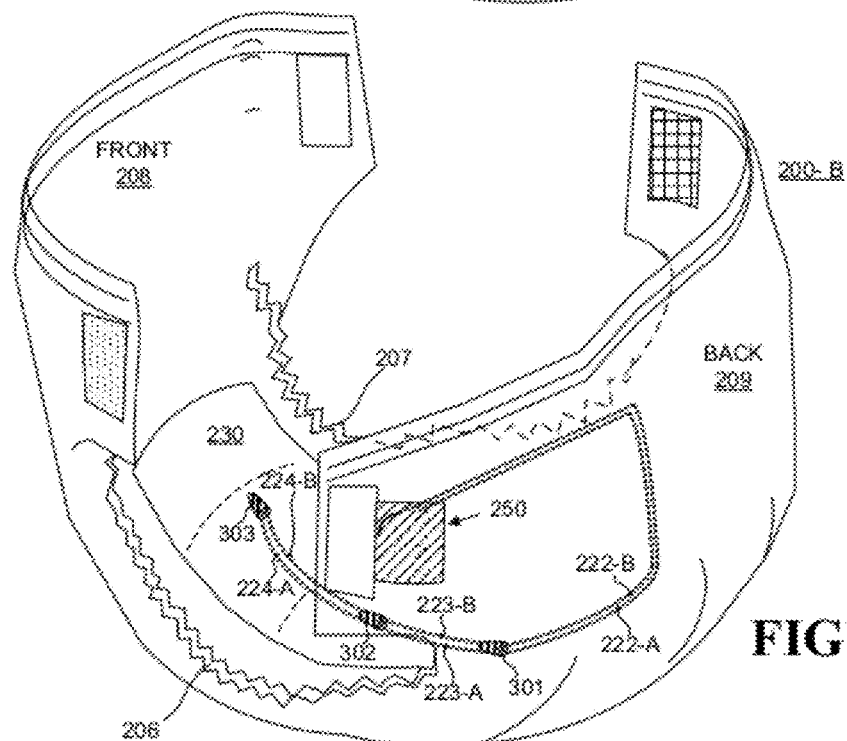
FIG. 2B is an isometric view of a diaper with a moisture detection system having a plurality of moisture sensors, according to one or more embodiments.
Figure 2C:
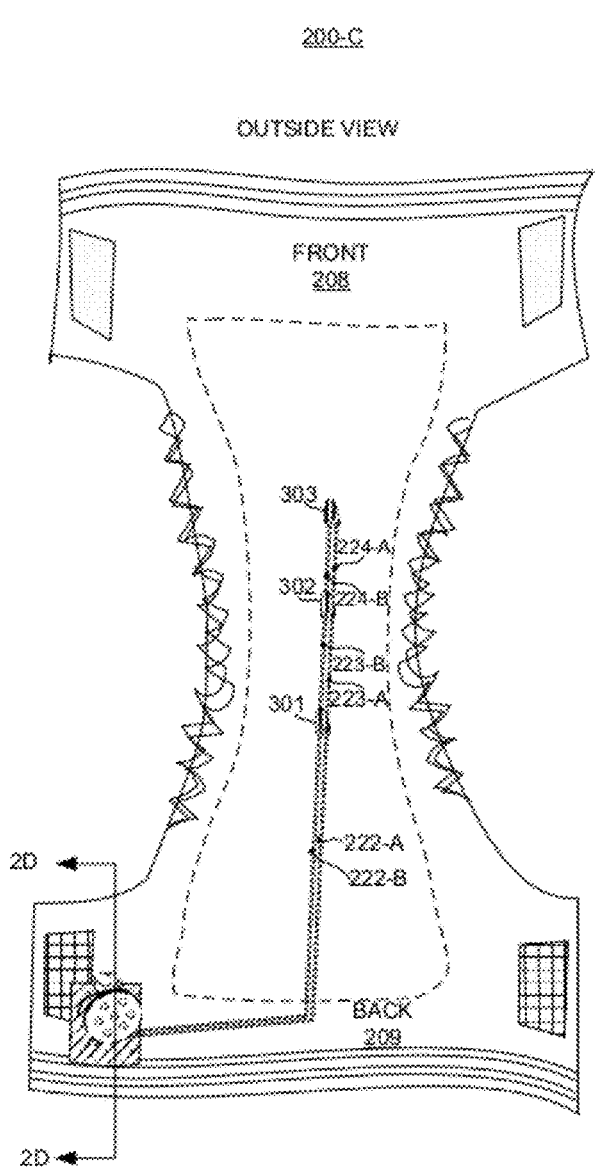
FIG. 2C is a top view of a diaper laid flat with a moisture detection system having a plurality of moisture sensors located therein, according to one or more embodiments.

Referring now to FIGS. 2B and 2C, an isometric view of a diaper 200-B and a view of the outside of a diaper laid flat 200-C, respectively, with a moisture detection system having a plurality of moisture sensors is shown, according to one or more embodiments. In particular, diaper 200-B includes a plurality of moisture sensors, e.g., three sensors 301, 302, and 303, disposed in one or more different locations in the diaper as shown, that are coupled to alarm system 250 in series, e.g., daisy-chained via leads 222-A, 222-B, 223-A, 223-B, 224-A, 224-B, wherein any one of the plurality of moisture sensors 301, 302, and 303 can independently activate a single alarm indicator in alarm system 250, e.g., a single tone, due to detection of moisture. In another embodiment, each of the plurality of moisture sensors 301, 302, and 303 has one or more different locations in the diaper as shown, and is separately coupled via electrically conductive leads, in parallel to a unique alarm indicator, illustrated in subsequent figure for alarm schematic, to thereby provide a unique alarm indication, e.g., audio, tactile, visual, data, wireless signal, etc., to indicate a specific location in the diaper that has moisture event, or to indicate a specific type or quantity of fluid or discharge from the user per the specific design of the sensor. One or more sensors 301-303 are disposed along a midline of diaper 200-B as that is the location from which the user is likely to discharge urine, feces, menses, or other bodily fluids and solids. Also, locating sensors along midline is less likely to cause a discomfort from user sitting while wearing diaper 200-B, as the gap between the left and right gluteus tissue, and the left and right ischial tuberosity bony structure of the pelvis creates a natural space to accept placement of a sensor. Also, the size of the sensor is sufficiently small to avoid detection.

For example, a vibrating tactile alarm coupled to sensor 302 and/or 303 located in the front 208 of the diaper to indicate the presence of moisture that is more likely to be urine, and an audio alarm coupled to sensor 301 and/or 302 located closer to the back, or rear, of the diaper to indicate the presence of moisture that is more likely to be feces. Similarly, a large discharge could cause multiple sensors to change state and trigger multiple different alarm indicators. In another embodiment, different moisture sensors can have different levels of moisture-sensitivity to indicate severity or extent of moisture in the proximity of the sensor. That is, by varying a design factor that changes how quickly the moisture sensor will undergo dimensional changes in the presence of varying degrees of moisture, or the threshold of moisture for which will trigger a reliable and sufficient dimensional change, in order to change the state of the electrical contacts, e.g., from open to closed, will provide alternatives for diaper design or product marketing for different user applications, e.g., for not sending an alarm for spot urination, but sending an alarm for a major urine discharge, or for other factors such as potty training scenarios, for adult bladder leaking or incontinence, etc. An exemplary design factor that would change the different level of moisture sensitivity of the moisture sensor include use of different materials, wall thicknesses and permeability factors in the moisture sensor such as an optional casing over the sensor, the material of which the moisture sensor housing is made, etc. Section 2D-2D illustrates a cross-section or a portion of alarm and surrounding diaper.

Figure 2D:
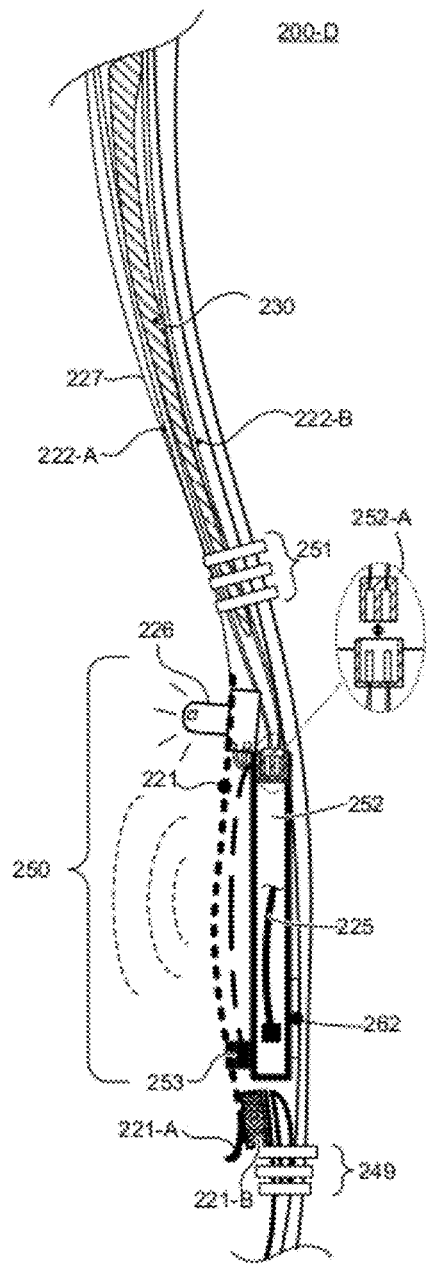
FIG. 2D is a cross-section view of a portion of the diaper having an alarm system responsive to the moisture sensor, according to one or more embodiments.

Referring now to FIG. 2D, a cross-section view of a portion of the diaper 200-D, taken from FIG. 2C, having an alarm system responsive to the moisture sensor is shown, according to one or more embodiments. Banding 249 and 251 is used on different layers of diaper 200-D to secure absorbent pads 230, electrical leads 222-A and -B, alarm system 250 including visual alarm indicator 226, reset button 253, and audio alarm indicator 252. Banding can include ultrasonic welding, adhesive such as glue, threaded stitching, or other means to maintain an bond across the different layers, such as moisture-proof backing layer 201, and other components of diaper 200-D. Outer cover 221 of alarm system 250 is shown as a flexible pocket embodiment with free edge 221-A of pocket 221 having optional hook and loop fastener 221-B selectively coupled to diaper backing layer 201 to more positively retain and allow selective access to interchangeable alarm system 250. Selectively detachable wire coupling 252-A provides a male/female coupling of wires or strips to allow alarm system 250 to be detached from a given soiled or damaged diaper and transferred to a fresh diaper, thus reducing cost of the alarm system to the user over the span of many diaper uses. Coupling 252-A can be a nominal-fitting coupling without hermetic sealing or it can optionally be a hermetically sealed coupling, e.g., via snug fit, o-ring, or seal using a flexible material such as rubber or fluourosilicon, in order to resist moisture. Button battery 262 provides power for alarm system 250 and optional antennae 225 is used to communicate to receiver base station.

Figure 2E:
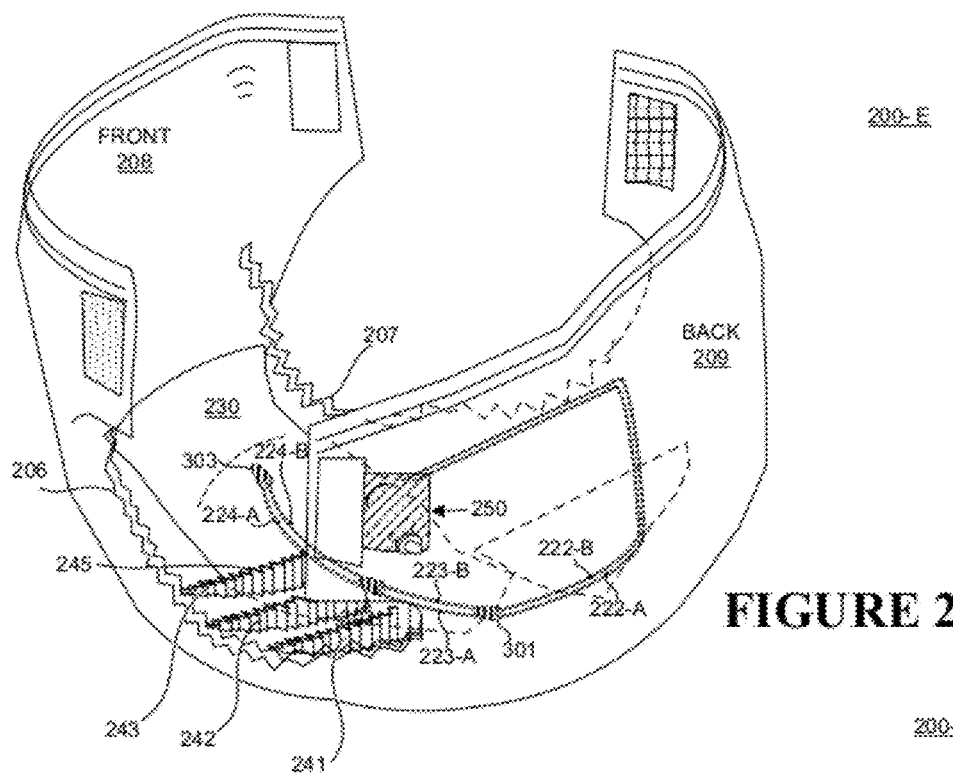
FIG. 2E is an isometric view of a diaper with a moisture detection system having a plurality of moisture sensors and having a transverse baffle, according to one or more embodiments.
Figure 2F:
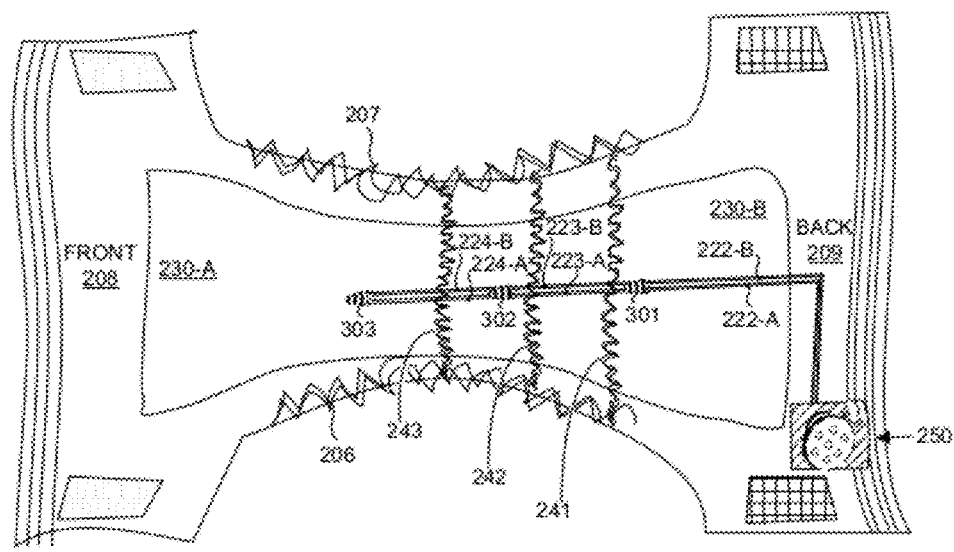
FIG. 2F is a top view of a diaper laid flat with a moisture detection system having a plurality of moisture sensors and having transverse baffles, according to one or more embodiments.

Referring now to FIGS. 2E and 2F, an isometric view of diaper 200-E and a top view of diaper 200-F laid flat, respectively, with a moisture detection system having a plurality of moisture sensors 301, 302, and 303, and having a plurality of transverse baffles 241, 242, 243 is shown, according to one or more embodiments. Diaper 200-F shows transverse baffles 241, 242, and 243 more fully, spanning transversely across crotch area of diaper 200-F located approximately as the area between leg openings 206, 207, and disposed over absorbent pad 230-A and 230-B, all contained by an outside layer of moisture-resistant material that is a shell. FIG. 2E uses a one-piece absorbent pad 230 that spans from front to back of diaper in the present embodiment, while FIG. 2F shows a two-piece absorbent pad, with front and back absorbent pads 230-A and 230-B that "butt up," overlap, or are attached to each other, in the proximity of one of the baffles 241-243, and with or without a moisture proof separator layer therebetween. Having separate front and back absorbent pads 230-A and 230-B allows control of cross-absorbency from front 208 to back 209 of diaper 200-H for purpose of alarm segregation to the region in which moisture exists, e.g., either to the front or back of a diaper.

Baffle sheets 241, 242, and 243 are arranged in parallel and coupled transversely across the crotch portion of the diaper from the first leg opening to the second leg opening and have a top uncoupled edge, e.g., 245, having an elastic member, e.g., elastic cord, etc. therein. Baffle sheets 241, 242, and 243 can be made of a moisture resistant stay-dry wicking material such as: polyester to allow some breathability when placed against the skin of the user, or can impermeable to fluids for a more effective barrier. In particular, first and second baffle, 241 and 242, help trap fecal matter there between in order to focus the resultant moisture on first moisture sensor 301 for purposes of detection and in order to resist fecal matter from propagating up the back 209 of diaper 200-F and the buttocks, or from propagating forward to sensitive genitalia of the user. Similarly, third baffle sheet 243 is intended to trap urine from males toward the front 208 of diaper 200-E and focus resultant moisture on third moisture sensor 303, whereas the combination of third baffle sheet 243 and second baffle sheet 242 is intended to trap urine from females closer to the urethra. The position and placement of baffle sheets can be tailored for a specific application and can be limited to a single or a plurality of baffle sheets 241-243.

Figure 2G:
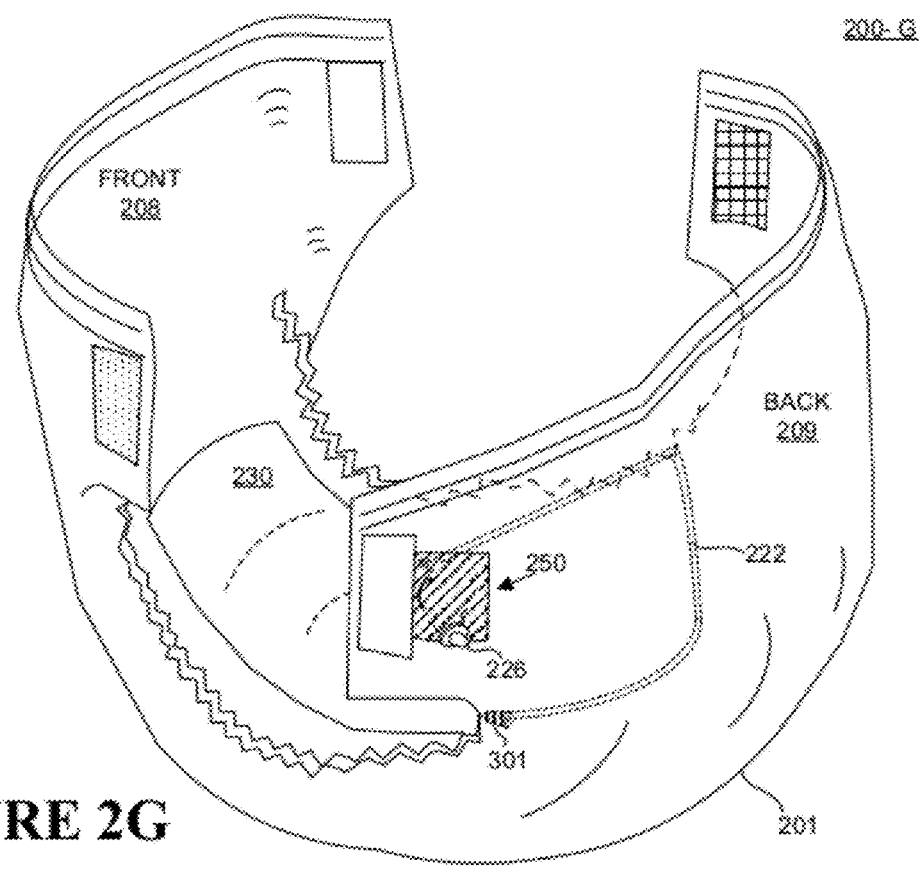
FIG. 2G is an isometric view of a diaper with a moisture detection system having a moisture sensor coupled to the alarm by wire leads, according to one or more embodiments.

Referring now to FIG. 2G, an isometric view of a diaper 200-G with a moisture detection system having a moisture sensor 301 using a pair of wire leads 222 to couple to the alarm is shown, according to one or more embodiments. Wire leads 222 can be adhesively attached to absorbent pad 230, shell 201, or other part of diaper 200-G or simply routed within one of multiple layers of materials that together comprise diaper 200-G.

Referring now to FIGS. 2H and 2I, a top and section view 2I-2I, respectively, of a diaper 200-H laid flat with a moisture detection system having a plurality of moisture sensors 301, 302, and 303 located therein that are separated by a transverse impermeable separator 272 is shown, according to one or more embodiments. Diaper has: a front portion 208, or front face that corresponds to the front, or anterior, of the user; a back face, or a back portion 209 that corresponds to the rear, or posterior, of the user; leg openings 206, 207; and is comprised of a first absorbent pad 230-A disposed towards the front portion 208 of diaper 200-H for absorbing urine; and a second absorbent pad 230-B disposed towards the back 209 of diaper 200-H for containing or absorbing feces, wherein the first absorbent pad 230-A and second absorbent pad 230-B are designed for contact against the user's skin; a moisture-resistant barrier 272 disposed between the first absorbent pad 230-A and the second absorbent pad 230-B to prevent urine from triggering a sensor disposed closer to the second absorbent pad, e.g., sensor 301 originally intended for detecting feces; and an outside layer, or shell, 201 of impermeable, or moisture-resistant, material that contains the first and second absorbent pad.

One function of moisture-resistant barrier 272 of FIGS. 2H and 2I and baffles 241, 242, and/or 243 of FIGS. 2E and 2F is to provide a barrier between sources of urine and sources of fecal matter, with the latter being more caustic to the wearer's skin, and thus, detection of the latter being more important in one embodiment. To avoid false positive alarms of a fecal detecting moisture sensor from a urine discharge, the baffles or barrier help to segregate urine away from a moisture sensor sensitive to, and/or located proximate to the discharge area of, fecal matter.

Moisture resistant barrier 272 is non-permeable, or impermeable, to fluids in one embodiment made of a plastic or polyurethane laminate (PUL) that physically separates first and second absorbent pad 230-A, 230-B, respectively. Alternative barrier 272 can be a portion of absorbent pad doped or impregnated with non-absorbent material like PUL during manufacturing, that virtually separates absorbent pad into two portions 230-A and 230-B. If plurality of sensors 301-303 are wired separately then they can detect different types or locations of moisture, e.g., 301 wired for detecting fecal deposition, while sensor 302, 303 are grouped together for detecting urine deposition, as shown in views and schematic of subsequent figures. Leads 222-A and 222-B can either be sealed as they traverse through or on either side of moisture-resistant barrier 272. Location of moisture resistant barrier 272 vis-à-vis moisture sensors and front 208 and back 209 portion of diaper 200-H can be any reasonable location in diaper to effectuate an accurate proximity detection of moisture.

Moisture Sensor

Figure 3A:
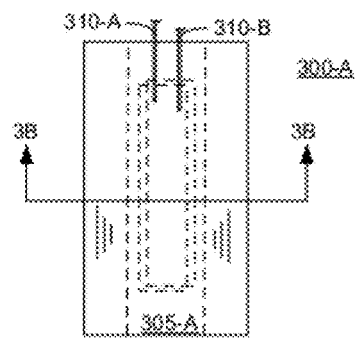
FIGS. 3A-3B are a top and cross-section view, respectively, of a moisture sensor having a round cross-section, open ends, and normally open electrical contacts in a dry state, according to one or more embodiments.

FIGS. 3A through 4Z illustrate oblique, orthographic, and cross-section views of various alternative embodiments of moisture sensors and of electrical contacts for the present disclosure. Referring now to FIGS. 3A and 3B, a top and cross-section view 3B-3B, respectively, of a moisture sensor 300-A having a round cross-section, open ends, and normally open electrical contacts 316-A and 316-B spaced apart by a distance 307, in a dry state is shown, according to one or more embodiments. Moisture sensor 300-A, used for detecting moisture in a diaper in one embodiment, is comprised of a housing 305-A with an outer surface 311 and/or a cavity having an inner diameter 312 formed therein, a plurality of electrically conductive contacts 316-A, 316-B disposed on or in housing 305-A, e.g., any combination of surfaces such as the outer surface, e.g., outside diameter 314, and/or on an inner surface, e.g., inside diameter 312, of cavity in housing 305-A, are selectively coupled to, or decoupled from, each other as a result of a dimensional change of housing 305-A arising from a change from a dry state to a moist or wet state when moisture sensor 300-A comes into contact with moisture. An electrical signal routable through the plurality of electrically conductive sensor leads 310-A, 310-B monitors a state, e.g., open or closed, of the electrically conductive contact circuit, e.g., wires or strips 310-A, 310-B that activates a local or remote alarm, e.g., 250 of FIG. 2A, to indicate the presence of moisture. The plurality of electrically conductive contacts 316-A, 316-B can either be initially disposed apart from each other in a substantially dry environment to represent a normally open circuit that does not activate a moisture alarm, or alternatively can be initially disposed against each other in a substantially dry environment to represent a normally closed circuit that does not activate a moisture alarm. A change in either of those normal states would trigger the alarm. Thus the moisture sensor 300-A detects moisture in a diaper by changing the state of electrical contacts as a result of the force and displacement from mechanical expansion or contraction of the moisture sensor 300-A in the presence of moisture.

Housing 305-A is formed into a shape that can have any geometry, e.g., having a cylindrical, oval, or rectangular cross-section. While sensor housing 305-A in the present embodiment is symmetrical, e.g., coaxial cavity inside diameter 312 and outer surface 311, the present disclosure is well-suited to any shape, such as an asymmetric shape, e.g., off-center geometries, for directional sensitivity. Furthermore, housing 305-A can be any dimension, e.g., length, height, width, diameter, aspect ratio, etc., that would provide stability for holding the contacts, and would be sufficiently small to not irritate the user of a diaper or garment containing the sensor while sufficiently sensitive to detect moisture. The smaller the sensor housing 305-A the lower the cost of materials, while allowing an option for using greater quantity of sensors for a diaper application, e.g. to provide a more sensitive and accurate detection of moisture, or to prevent a false positive alarm from one failed or unintentionally activated sensor. Desirable shapes and dimensions of housing 305-A are those that are less apparent or obtrusive to the wearer of a garment containing the moisture sensor, or those that are more rigid and robust in a dry state, and/or those that are more responsive and consistent in the dimensional changes, and consequently the change in status of the circuit, in the presence of moisture.

Material for any of the moisture sensor housing configurations is electrically insulative and dimensionally-sensitive to the presence of moisture, e.g., housing 305-A will expand or contract in the presence of moisture sufficient to affect a change in the state of the electrical contacts 316-A, 316-B. However, the material is dimensionally stable when dry, such that when housing, e.g., 305-A is in an essentially moisture free environment, e.g., without any liquid discharge from the user, then the housing and the contacts, e.g., 316-A, 316-B, remain essentially static in their normal state, e.g., normally open or normally closed. The material for the housing 305-A is also dimensionally stable in a nominal environment with body perspiration and humid ambient environments.

In one embodiment, the entire sensor device, e.g., sensor housing 305-A, is biodegradable. Biodegradable means the material is capable of being decomposed by biological agents, such as bacteria. In other embodiments, the sensor is only partially biodegradable or is non-biodegradable. Exemplary material used for sensor housing 305-A includes: cotton, viscous rayon, viscose staple fiber (VSF), hydrophilic biodegradable polyester, cellophane, polymer fibers such as polylactic acid, segmented linear polyurethanes, segmented cross linked polyurethanes, or any other material that has dimensional stability in a dry state and expands or contracts in a moist or wet state such that it could trigger a change in a circuit, or any combination thereof. A material that would constrict in moisture includes ones that are at least partially soluble in water or a specific type of user discharge, e.g., urine, blood, etc. For a sensor that operates by expansion, or swelling, of the material, a reasonably high amount of swelling is preferred since it will allow a more positive trigger in the presence of moisture. However, the material should not have uncontrolled continual expansion after triggering the system alarm coupled to the sensor, such that it would cause discomfort to a user. Thus, in one embodiment, a sensor material has a swelling rate of approximately 5% to 30%, e.g., cotton, in a different embodiment, the sensor material swelling rate is no less than 30%, while in another embodiment, the sensor material has a swelling amount of approximately 60%, e.g., VSF, while in another embodiment the sensor material has a swelling rate of approximately 130%, e.g., cellophane. A desirable amount of swelling for the sensor material can be any value in these ranges, e.g., 30-60%, 60-130%, at least 130%, etc. depending upon the configuration of contacts and placement of contacts in or on the sensor that is used and the amount of compressing of the material to form the sensor housing. The material for the sensor can be compressed or highly compressed during the manufacturing of the sensor to provide even greater increases in expansion than the base material, when exposed to moisture. For example, multiples of expansion in size is realized, in ranges of one to two times, two to three times, or more than three, but generally less than ten, times the sensor's original size. Any factor increase in the size of the sensor is useful for miniaturizing the moisture sensor and for providing a strong signal indicating the presence of moisture, with one limitation being that excessive expansion, e.g., beyond three to ten times original size, should not be so great as to cause irritation or discomfort to the wearer of the absorbent article.

The material for the housing undergoes a manufacturing process, described in subsequent FIG. 7A-7D, that compresses the material to a small and compact shape, e.g., to create a compressed viscose rayon in one embodiment. Compressing the material provides more of the material to react to moisture, which subsequently produces more dimensional change in the sensor, e.g., more expansion or contraction. Additionally, the compressed material of the sensor housing 305-A provides stiffness that substantially maintains the cavity surface 312 formed therein in order to maintain an open circuit without contacts 316-A, 316-B touching in a dry environment. Sensor device 300-A is a consumable one-time use device in the present embodiment. Material for sensor can be specific to the type of moisture absorbed, and be coupled to a unique alarm in order to indicate severity and/or type of discharge from user. Thus, for example, a fast expanding material in one moisture sensor located in a diaper location closer to the buttocks of the user for a lower moisture discharge from user, such as a non-diarrhea type of feces, could be coupled to a lower volume and less repetitive type of alarm. However, in another embodiment, material for housing has an expanding compound triggered by any acidic content of diarrhea, which would be coupled to a louder and more frequent alarm, because of the severity of the irritation and inflammation from the acidic diarrhea against the user's skin. The material and shape of a moisture detector can be tailored for any discharge from the wearer, including urine, feces, menses, bleeding and serous fluid from healing wounds, etc.

Descriptions provided for FIGS. 3A and 3B for: material selection for housing and electrical contacts; electrical circuit operation; other moisture sensor functions and operation, are practically applicable to moisture sensors, housings, and electrically conductive apparatus discussed in alternative embodiments hereinafter.

Figure 3C:
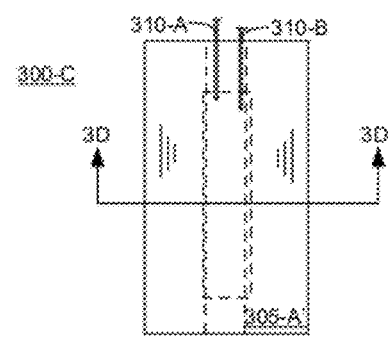
FIGS. 3C-3D are a top and cross-section view, respectively, of a moisture sensor having a round cross-section and closed electrical contacts after swelling from the presence of moisture, according to one or more embodiments.
Figure 3B:
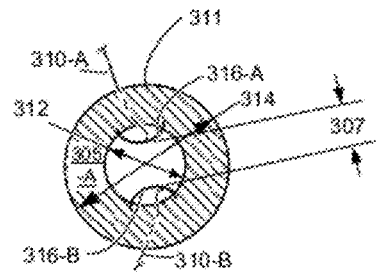
Figure 3D:
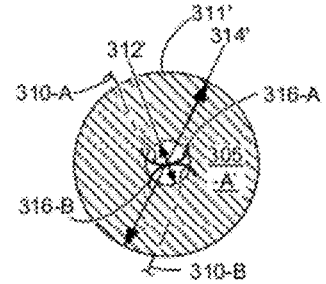

Referring now to FIGS. 3C and 3D, a top and cross-section view 3D-3D, respectively, of a moisture sensor 300-C with housing 305-A' having the round cross-section and open ends, after swelling from the presence of moisture and consequently closing the electrical contacts 316-A, 316-B to communicate a signal indicating the presence of moisture is shown, according to one or more embodiments. Specifically, in the presence of moisture, outer surface 311' of housing 305-A' swelled and/or expanded to outside diameter 314' while the cavity 312' formed therein collapsed, contracted, or closed up, to inside diameter 312', which is less than the dry state inside diameter 312, in order to close contacts 316-A, 316-B, e.g., to close the circuit, and thereby provide a change in an electrical signal, which consequently indicates the existence of the moist or wet environment. The convex design of contacts 316-A, 316-B allows for contact on the crown of the convex surface, thereby accommodating for distortion and misalignment, and providing for spring force contact between contacts 316-A, 316-B as they are pushed together by the swelling housing 305-A'. In another embodiment, depending upon the circuitry, the physical placement of the electrical contacts, and the behavior properties of the material, a cavity can dilate in the presence of moisture, and open a normally closed circuit. In particular, the dimensional change to the housing of the moisture sensor can be in one or more dimensions, e.g., the housing can expand linearly only along the axis of the cylinder; can expand linearly and radially; can expand radially but not linearly; or can expand in 2-3 axes, e.g., all dimensions. The weave design and material choice of the moisture expanding material can be non-directional. Alternatively, the weave, fiber, or cell orientation of the housing material can have a directional preference, e.g., a radial fiber or cell orientation, for moisture absorbance, and thus a directional preference for dimensional change, e.g., the radial dimension change can be significantly more effective than say the axial dimension change of the housing. In another embodiment, the outer surface of the housing can contract. For the expanding configuration, the material of moisture housing 305-A' can remain in its expanded state, thus leaving the moisture sensor 305-A' continuously in the 'tripped' or activated circuit state.

Figure 3E:
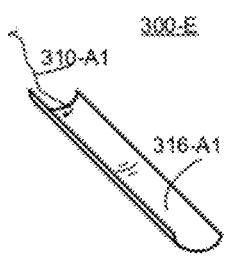
FIGS. 3E-3F are oblique views of a convex contact for use in the moisture sensor housing, having a wire lead or strip lead, respectively, according to one or more embodiments.
Figure 3F:
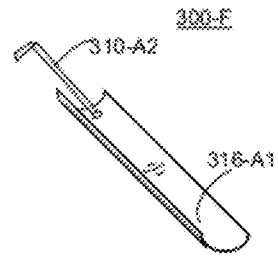

Referring now to FIGS. 3E and 3F, isometric views 300-E and 300-F, respectively, of a convex contact 316-A1 for disposing in the moisture sensor, having either a wire lead 310-A1, or a strip lead 310-A2, respectively, is shown according to one or more embodiments. Wire lead 310-A1 and strip lead 310-A2 corresponds to strip lead 222-A and to wire lead 223-A, respectively, in diaper assembly 200-B of FIG. 2B. Contact 316-A, as well as mating contact 316-B, is a metallic or non-metallic conductor that will communicate an electrical signal from a power source back to an alarm system, as illustrated herein. In one embodiment Strip lead and wire can have insulation or if have no insulation, then rely on adhesives or electrically non-conductive materials in the garment, e.g., diaper, to surround the wire or lead and provide the insulation function. In one embodiment, metal conductors used in a diaper are of the same material to avoid a galvanic action which creates corrosion and a slight electrical charge. In another embodiment, using dissimilar metals is not an issue, as the lifespan of the diaper during its use, where it is likely to be exposed to moisture, is sufficiently short that galvanic action is not harmful or degrading to user or conductors and sensors. Another embodiment utilizes carbon nanotube conductive "wires" as a conductive non-metal material, made from sheets of graphene, e.g., having a circular cross-section like wire, or a flat cross-section like a strip. Its specific conductivity, the conductivity-to-weight ratio, surpasses copper and it is non-corrosive, making it ideal for a moist environment. Details on a carbon nanotube configuration for wiring is described in "Science and application of Nanotubes" By David Tomanek, Richard J. Enbody, Springer, 1 edition (Mar. 1, 2000), which is hereby incorporated by reference. Contact 316-B, shown in prior figs, has a design that minors that of contact 316-A.

Contacts 316-A and 316-B can have any shape and dimensions, such that they are compatible to fit within the respective shape and dimensions of housing 305-A, and can protrude from one or both ends of a housing, e.g., 305-A, or can be shorter, or substantially shorter, than length of a housing, in order to avoid accidentally being bent and contacting each other as a false positive signal. In the present embodiment, contacts have a curvature that is convex with respect to each other when disposed in housing 305-A. Contact material can be any conductive material such as those mentioned hereinabove for electrically conductive leads, e.g., metallic or non-metallic, which are soldered, crimped, ultrasonically welded or otherwise adhered thereto in a manner that permits electrical conductivity. Contacts, e.g., 316-A and 316-B, are disposed in housing 305-A via adhesive or by mechanical retention, such as being concurrently incorporated in the sensor housing material during housing fabrication.

Figure 3G:
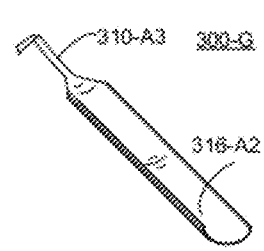
FIG. 3G is an oblique view of an alternative embodiment of a continuous lead and contact, according to one or more embodiments.

FIG. 3G illustrates an alternative embodiment of a continuous lead and contact 300-G, in accordance with one or more embodiments. Specifically, lead 310-A3 and contact 316-A2 are made from a single continuous conductor. A metal or electrically conductive polymer, with or without doping, can be formed at the end to create the desired shape and contour of the contact 316-A2, e.g., by stamping or drawing, and additional treatments, e.g., curing or work hardening. Being constructed from a single piece, problems with a lead and contact connection, such as breaking, will be minimized, and the system as a whole will be more reliable.

Figure 3H:
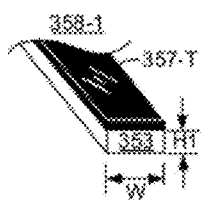
FIGS. 3H, 3I, and 3J are oblique views of a conductive polymer lead, in accordance with one or more embodiments.
Figure 3I:
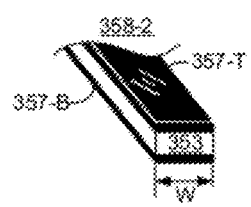
Figure 3J:
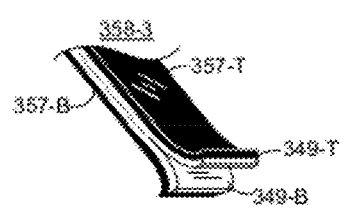

Referring now to FIGS. 3H, 3I, and 3J, a conductive polymer lead is shown, in accordance with one or more embodiments. Leads 358-1 is a single-sided lead constructed from a wide sheet of the polymer 353 (not shown), that is doped, coated, or painted with a conductive material, e.g., ink, on one side to form an electrically conductive surface 357-T and then cut into narrow strips of height H1 and width W, having a stable aspect ratio of H1/W, to form the leads. In an alternative embodiment, leads 358-2 and 358-3 are double-sided to produce multiple leads in a single-body construction. Leads are formed by starting with a wide sheet of electrically insulative polymer that is doped, coated, or painted with a conductive material on both sides to form multiple electrically conductive surfaces 357-T and 357-B that are insulated from each other by the polymer substrate. The product is cut into narrow strips as leads. After cutting into strips, a single body 358-2 or 358-3 will have both conductors thereon, one on the top face 357-T and one on the bottom face 357-B, with the insulative substrate 353 therebetween. An optional coating step can follow any of these lead designs to provide an outer insulative layer. In one embodiment, the end of the lead can be cut along the midplane polymer sheet, to reveal two separate leads 349-T, 349-B, with conductive faces and a portion of the insulative substrate for subsequent mechanical or conductive-adhesive coupling to the contacts in the moisture sensor. One embodiment of conductive material is conductive ink with carbon or other types of filler supplied by Creative Materials Inc. of Tyngsboro, Mass. Further, contacts could be formed at the ends by stamping, drawing, molding, or forming the desired contour of the contact, and optionally using heat and/or organic compounds, such as bisphenol A (BPA) to create and maintain the shape of a contact, e.g., concave as shown in other figures.

Referring now to FIGS. 3K and 3L, a top and cross-section view, respectively, of a moisture sensor 300-K with a housing 305-K having a round cross-section 3L-3L, and a first end that is closed 322-K and a second end 324-K that is open, with no outer casing is shown, according to one or more embodiments. In particular, moisture sensor 300-K allows for the insertion of contacts 316-K and 316-L with contacts 310-A and 310-B through open end 324-K, yet has a closed end 322-K for ease of insertion and increased radial rigidity, e.g., for resistance to crushing under load of the user, which feature is typical for FIGS. 3K-3P.

Referring now to FIGS. 3M and 3N, a top and cross-section view 3N-3N, respectively, of a moisture sensor 300-M with a housing 305-M having a round cross-section 3N-3N, one closed end 322-M and one open end 324-M, with a mesh casing 325 around the outside diameter 314 is shown, according to one or more embodiments.

Moisture sensor 300-M includes an outside layer 325 disposed around the housing 305-M, wherein the outside layer 325 promotes the retention of the housing shape, in one embodiment. Outside layer 325 is a fibrous material disposed on the outer surface of the moisture-expanding material in order to inhibit expansion of the outer surface of the moisture-expanding material thereby promoting closure of the cavity inside the housing. The fibrous material is a mesh, a net, sleeve, a sheet, a weave, or a winding of organic or inorganic material such as a nylon or polyester mesh, or any material that would allow penetration of moisture to housing 305-M while providing compression resistance against an expanding housing 305-M in a dry or moist environment or state. Similarly, FIG. 3O and FIG. 3P illustrate a top and cross-section view 3P-3P, respectively, of a moisture sensor 300-O with a round cross-section housing 305-O, one closed end and one open end, with a continuous casing 327, sleeve, or sheet, around the outside is shown, according to one or more embodiments.

Referring now to FIGS. 4A and 4B, a top and cross-section view, respectively, of a moisture sensor 400-A with a round cross-section, open ends, with a two-axis hourglass-shaped cavity is shown, according to one or more embodiments. Moisture sensor 400-A includes: housing 350-A with double hourglass shape cavity, having two sides with a first radius 340 and two sides with a second radius 342; contacts 317-A and 317-B disposed therein and leads 310-A and 310-B coupled thereto, respectively. Contacts 317-A and 317-B obliquely illustrated in FIG. 4C mate into two-axis hourglass-shaped cavity, i.e., an hourglass shape in both in both dimensions, in sensor housing 350-A, having first radius 340 such that contacts 317-A and 317-B are trapped in double hourglass geometry by virtue of the trapped corners of the hourglass shape having narrow width 354-A and wide width 354-B and short height 356-A and tall height 356-B, according to one or more embodiments.

Referring now to FIGS. 4D, 4E and 4F an oblique view, top view, and front view, respectively, of a moisture sensor 400-D with a rectangular cross-section, and both open ends is shown, according to one or more embodiments. Rectangular moisture sensor 400-D has housing 352 has a rectangular shaped cavity with width 359-A greater than height 351-A, coaxially located within outside rectangular shape of housing 352 having length 355 greater than width 359-B greater than height 351-B. Alternatively, these relative size relationships can be changed wherein, for example, width 359-B is greater than length 355. In that embodiment, housing 352 can lay flat, similar to a thick washer with correspondingly reduced size contacts, within the diaper, and allowing cavity to be facing the user for acceptance of urine or feces, which will thereby make sensor more responsive. Contacts 361-A and 361-B are embedded, adhesively or mechanically coupled within cavity width 359-A and height 351-A as shown such that crown of contacts 361-A and 361-B are approximately aligned and spaced apart from each other for the normally open circuit. Benefits from using a rectangular cross-section moisture sensor include: a flatter profile and thus less potential for protrusion and discomfort for user; better retention ability in the diaper on a wider 359-B top surface; better crush strength, from the shorter side surface of height 351-B. Referring now to FIG. 4G, an isometric view of a contact 361-A for disposing in the moisture sensor housing is shown, according to one or more embodiments. Contact 361-A has a crown 363 that can self-center against mating contact in housing, e.g., housing 352.

Figure 4H:
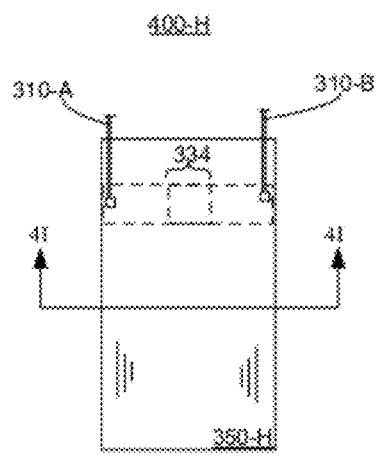
FIGS. 4H and 4I are a top and cross-section view, respectively, of a solid round cross-section moisture sensor in a dry state, according to one or more embodiments.
Figure 4J:
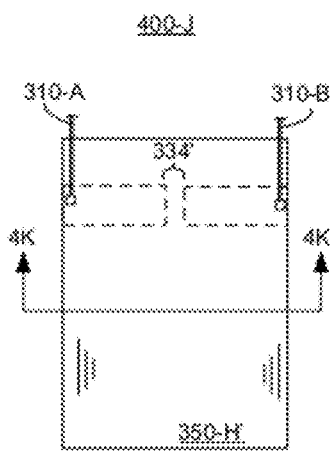
FIGS. 4J and 4K are a top and cross-section view, respectively, of a solid round cross-section moisture sensor in a moist and expanded state, according to one or more embodiments.
Figure 4I:
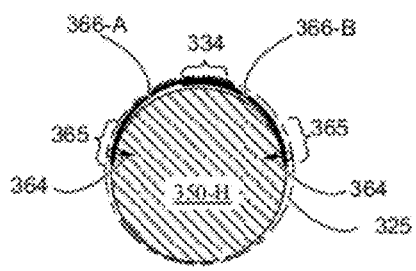

Referring now to FIGS. 4H and 4I, a top and cross-section view 4I-4I, respectively, of a moisture sensor 400-H with a solid round cross-section housing 350-H, having normally closed exterior contacts 366-A and 366-B, in a dry state is shown, according to one or more embodiments. Contacts 366-A and 366-B have a circular shape, conformal to circular cross-section, that are retained at one end in solid round cross-section housing 350-H via fasteners, e.g., a barbed pin 364, or adhesive over an area 365, while and at the other end, having a freely sliding overlap 334 area, where contacts 366-A and 366-B have contact against each other, but can slide apart tangentially. An optional mesh or cover 325 can be disposed over housing 350-H and contacts 366-A and 366-B in order to maintain relative position and overlap 334 of contacts 366-A and 366-B. Optional outer sleeve 325 configurations, such as described in FIG. 3M, can be used to maintain shape of housing, 350-H, and to maintain surface contact between contacts 366-A and 366-B and to prevent damage to contacts 366-A and 366-B such that they are not displaced from housing 350-H from movement of user and movement of layers in diaper assembly.

Figure 4K:
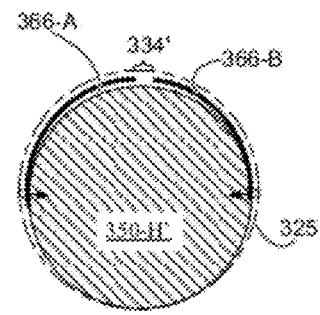

Referring now to FIGS. 4J and 4K, a top and cross-section view 4K-4K, respectively, of a moisture sensor 400-J with a solid round cross-section housing 350-H', having normally closed exterior contacts 366-A and 366-B in a moist and expanded state is shown, according to one or more embodiments. Because housing 350-H' expands in the presence of moisture and because contacts 366-A and 366-B are retained at one end, then the overlapped and unretained ends slide against each other until the overlap area becomes a gap 334', thus changing the state of the moisture sensor 400-J to an open state.

Figure 4L:
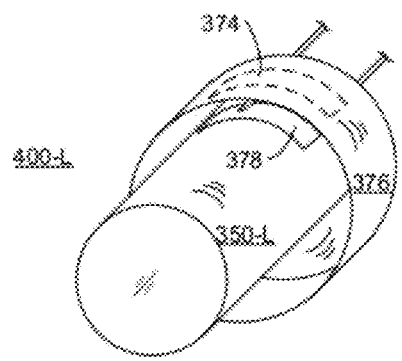
FIG. 4L is an oblique view of a solid round cross-section moisture sensor in a dry state with a having an external contact on its outer diameter, according to one or more embodiments.
Figure 4M:
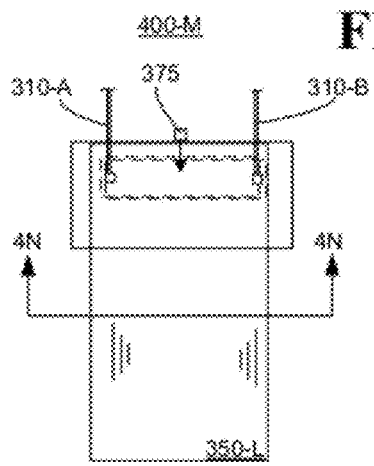
FIGS. 4M and 4N are top and cross-section view, respectively, of a solid round cross-section moisture sensor in a dry state, according to one or more embodiments.
Figure 4O:
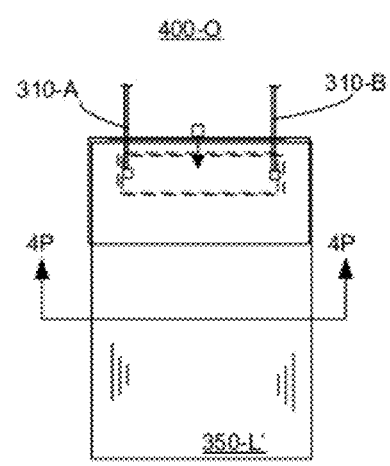
FIGS. 4O and 4P are a top and cross-section view, respectively, of a solid round cross-section moisture sensor in a moist and expanded state, according to one or more embodiments.
Figure 4N:
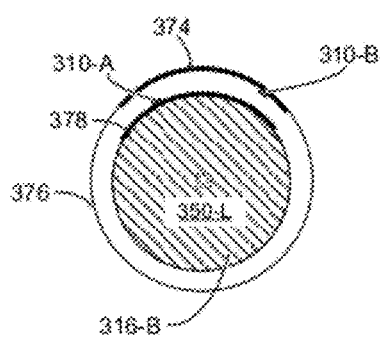

Referring now to FIGS. 4L, 4M and 4N an oblique view, a top view, and a cross-section view 4N-4N of a moisture sensor 400-L in a dry state with a solid round cross-section having an external contact 378 adhesively disposed on its outer diameter, partially enclosed in an oversized shroud 376 with a contact 374 adhesively disposed in its inside diameter, is shown, according to one or more embodiments. Shroud 376 is sufficiently rigid and retained by barbed pin 375, and/or by adhesive, to housing 350-L that it does not crush under load from a user to create a false positive of contacts 374 and 378 touching when the moisture sensor is in a dry state.

Figure 4P:
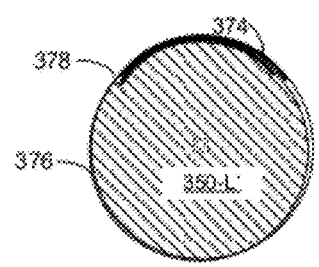

Referring now to FIGS. 4O and 4P, a top and cross-section view 4P-4P, respectively, of the moisture sensor 400-O in a moist and expanded state with a solid round cross-section having an external contact 378 on its outer diameter, partially enclosed in an oversized shroud 376 with a contact 374 on its inside diameter is shown, according to one or more embodiments. Shroud 376 does not extend more than nominally along length of axis of housing 350-L so as to avoid blocking moisture sensor from moisture provided from user.

Referring now to FIG. 4Q, an oblique view of a moisture sensor 400-Q with an oval cross-section is shown, according to one or more embodiments. Oval housing 350-Q has a width of 379 which is greater than height 380 in order to provide a lower profile sensor that will be less apparent and less irritating to a wearer of a diaper. A two-axis hourglass cavity formed by housing 350-Q is similar to that described and illustrated in FIGS. 4A-4C, and contacts 316-A and 316-B disposed against top or bottom radius 360 of cavity.

FIG. 4R through 4S, are oblique views of a saw tooth plate moisture sensor 400-R, according to one or more embodiments. The saw tooth plate portion 383 is a mating shape for top plate 381-A and bottom plate 381-B with height h1 separated by filler plate 382 of height h2 Filler plate 382 materials are described hereinabove to expand or contract when exposed to moisture such as urine or loose, watery stool. Height h1 is less than thickness or height h2 for a normally closed system, with plate 382 comprised of an expanding material in the presence of moisture, while height h1 is greater than thickness or height h2 for a normally open system, with plate 382 comprised of a dissolving or contracting material in the presence of moisture.

Referring now to FIG. 4T through 4Y, three different embodiments of clamshell moisture sensors 400-T, 400-U, 400-V, 400-W, 400-X, and 400-Y are shown, according to one more embodiments, that use materials described hereinabove to expand or contract. FIGS. 4T through 4W use a cylindrical sensor material 390 trapped in a top and bottom clamshell halves 386-A and 386-B and sides 386-C with pressure maintained by spring band 387 retained thereto and use contacts 385-A and 385-B to close or open a circuit. Clamshell halves are made of conductive material that form a portion of an alarm circuit, where clamshell halves 386-A and 386-B are covered by an insulator, e.g., plastic insulator, on all sides except faces of contact plates 385-A and 385-B, whether full width or half-width configuration, that is coupled, e.g., via leads (not shown), to an alarm system, e.g., as shown in subsequent FIGS. 5A-5C. Thus, FIGS. 4T and 4V represent a normally open system with contacts 385-A and 385-B spaced apart by distance G1 when sensor material 390 is in a substantially dry state. In contrast, FIGS. 4U and 4W represent a normally closed system with contacts 385-A and 385-B contacting each other when sensor material 390 is in a substantially dry state. The introduction of moisture causes the state of the sensor to change, e.g., from FIG. 4T to 4U or from FIG. 4V to 4W, or vice versa for a normally closed system. FIGS. 4X to 4Y illustrate a normally open circuit system utilizing a spherical or oval capsule 389 with dissolvable membrane made of polyvinyl alcohol (PVA) and filled with liquid oil or air, of sufficiently small volume to not be noticeable to wearer of diaper, when released. When exposed to moisture, e.g., urine, PVA membrane dissolves and contents are released, allowing clamshell halves 386-A and 385-B to contact each other, with exposed faces 385-A and 385-B closing an alarm circuit. In an alternative embodiment, spherical body 389 is a solid material, soluble in water, e.g., urine, such as polystyrene foam, or organic and more biodegradable starch-based foam, e.g., made from grain sorghum or corn starch.

Figure 4Z:
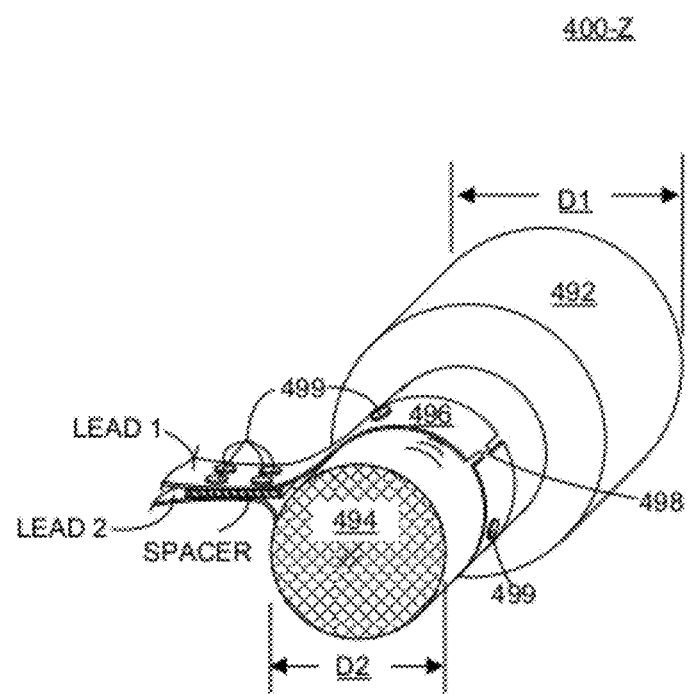
FIG. 4Z is an oblique view of a moisture sensor using a physical fuse to create an open circuit, according to one or more embodiments.

Referring now to FIG. 4Z, an oblique view of a moisture sensor 400-Z using a physical fuse to create an open circuit is shown, in according to one or more embodiments. Sensor 490 has a cylindrical body 494 with a nominal diameter D2 around which is wrapped a conductive lead 496 retained by non-conducting fasteners 499 and a non-conductive spacer to a set position and diameter. Larger diameter D1 cylindrical body 492 provides a protective shoulder to allow body 494 to expand and lead 496 to rupture in a moisture event. Conductive lead 496 has a physical fuse 498 with a substantially reduced cross-sectional area as compared to the balance of the lead. The physical fuse 498 is disposed on the circumference of body 494, such that when a moisture event occurs, and body 494 swells due to its moisture absorbing properties, leading to the rupture or shear of physical fuse 498 to create an open circuit between lead 1 to lead 2, which are both electrically coupled to an alarm system. The cross-sectional area across physical fuse 498 is sized such that the product of it times the rated tensile strength of the lead material is less that a force exerted on it by a swollen and expanded sensor body 494.

The embodiments of sensors shown in FIGS. 3A-4Z can be of any size suitable to provide sensitivity to moisture, accuracy in true positive moisture sensing function, and comfort to wearer, e.g., without becoming a noticeable presence that might otherwise make an impression in the skin, or an irritation to a bone or a joint. Thus positioning of sensor 301, 302 and 303 is along the midline of the diaper, which would correspond to the median of the wearer of the diaper. The smaller the sensor, the less likely to be noticeable or of discomfort to the user, and the more likely it is to be crush proof from body weight placed thereon. Thus, in one embodiment, a larger size of sensor, e.g., several square centimeters to several square inches or more of outside surface area, with a lower quantity of sensors used in a diaper, will still provide a wide area over which moisture can be detected. In another embodiment, a higher quantity of distributed smaller sensors can be used with sensors having several square millimeters to several square centimeters of surface area. In one embodiment, a sensor had a 4 mm diameter, or width, and a 6 mm length. However, the present disclosure is not limited to any specific size or surface area of sensor.

Alarm

Figure 5A:
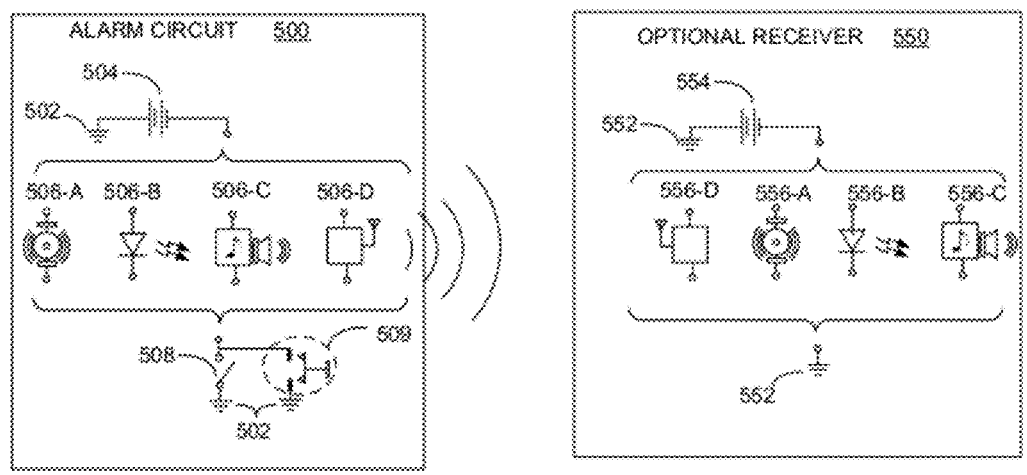
FIG. 5A is a schematic of an alarm circuit and optional wireless receiver circuit, with multiple optional alarm indicators to indicate the presence of moisture, according to one or more embodiments.

Referring now to FIG. 5A, a schematic of an alarm system circuit 500 and optional wireless receiver circuit 550, each with one of multiple optional alarm indicators for indicating the presence of moisture is shown, according to one or more embodiments. Alarm system 500 comprises: logic indicated in schematic having a normally open moisture sensor switch; a power source 504, e.g., button battery stored in audible alarm housing 262 of FIG. 2D, coupled to the logic. Alarm system 500, which is preferably reusable but optionally disposable, also includes an optional transmitter 506-D that signals to an optional remote receiver base station 550 when the alarm system is activated; and an alarm indicator coupled to the battery source and to moisture sensor switch 508, wherein the alarm indicator is any individual or any combination of alarms shown, e.g., an audio alarm indicator 506-C, a visual alarm indicator 506-B, a tactile alarm indicator 506-A, a wireless signal alarm indicator 506-D, e.g., having an optional data message output from built-in memory. Thus, both an audio and a visual alarm can be coupled to single moisture sensor switch 508 to provide a notice to user or guardian of user of a moisture occurring event in the diaper. Components are shown as individual components to illustrate the flexibility of combinations that can be coupled together as desired by designer. Receiver base station 550 can be a stationary unit with wall-plug, or a mobile battery-powered receiver.

In particular, visual alarm indicator 506-B can be a light emitting diode, a flashing light source, or some other display device that can change in visual appearance in order to distinguish a given user with a soiled diaper amongst a population of infants at a daycare facility all wearing diapers. Audio alarm indicator 506-C can alternatively include a prerecorded or a recordable message, such as a chime, a tune, a buzzer or a voice message that is played when the alarm is activated. The logic in the alarm system detects either a change from a normally open circuit to a closed circuit or from a normally closed circuit to an open circuit, as generated by the moisture sensor illustrated schematically as switch 508 coupled to ground 502. Optional wireless transmitter 506-D is coupled to battery 504 and to alarm system wherein the wireless transmitter 506-D has a preset or a programmable transmitter duty cycle in any of these ranges: less than 1%, between 0.1 and 1%, or between 1% and 10%, such as 5%, or any other safe and effective duty cycle above 10% but less than or equal to 50%, or greater than 50% for transmitting a signal to another device, e.g., an optional operation receiver having audio, visual, tactile, or data indicating means for an alarm, such as a remote receiver, or base station, alarm indicator. Transmitter 506-D is only strong enough in the present embodiment to transmit a reasonable distance, e.g., a house, yard, or a child care facility. Although the emission strength of the transmitter is very low, and thus not harmful, the lower duty cycle described herein reduces the exposure of any persons in the vicinity to electromagnetic radiation.

Wireless transmitter 506-D is reset to an off position after physically being reset on the diaper or on a receiver unit wirelessly coupled to the transmitter, e.g., after the diaper is soiled and the alarm has been removed therefrom. An optional operational indicator 509 is coupled to the alarm device in parallel with sensor 508 for indicating the operational status of the transmitter and/or the operational status of the battery source, e.g., 253 reset/operational indicator button in FIG. 2D. A handshake protocol can be used to send only a single signal from the diaper to a remote receiver base station, if the remote base station can acknowledge back to the alarm system in the diaper that the signal was received. Alternatively, a repeat signal can be transmitted periodically, e.g., once per minute or any other frequency, as preprogrammed or as user-programmed in a user-programmable transmitter. Low electromagnetic signal emission is important to many users or their guardians, in order to reduce or avoid any potentially harmful physiological effects from electromagnetic waves. Optional receiver 550 includes similar devices and layout as alarm circuit 500, namely power source 554, receiver 556-D, and one or more optional alarms, e.g., vibrating tactile alarm indicator 556-A, light emitting alarm indicator 556-B, audible alarm 556-C with same features as audible alarm 506-C, coupled to ground 552. In one embodiment, different diapers can have transmitters that transmit on different frequencies to communicate to the same receiver base station alarm receiver so that large numbers of diaper wearers can be tracked, e.g., in an institutional setting with multiple clients wearing diapers that otherwise rely on smell or the distress of a wearer to identify the problem. Different transmitters can undergo a pairing process with a receiver base station to tie them to a given alarm type representing a given user or application. By having a receiver base station receiver that can link or identify a given frequency with a given user, e.g., by a lookup table or some other form of marking or associating a frequency with a specific user, the detection of the soiled diaper and the wearer becomes immediately and directly identifiable.

Any of alarm indicators 506-A through 506-D can be designed to provide multiple types of alerts, e.g., after activation of a sensor, or an indication of low battery, and/or unit replacement for some other failure, via different modulation effects, e.g., quick audio, visual, or data signal for operational readiness, a steady on signal for low battery/replacement alert, and flashing light when fecal matter is detected, or any pattern desired. Transmitter can be a resusable unit with a removable/replaceable button battery under a tethered cover to avoid a choke hazard. Receiver 550 can be a durable unit with replaceable battery or wall-powered plug.

Figure 5B:
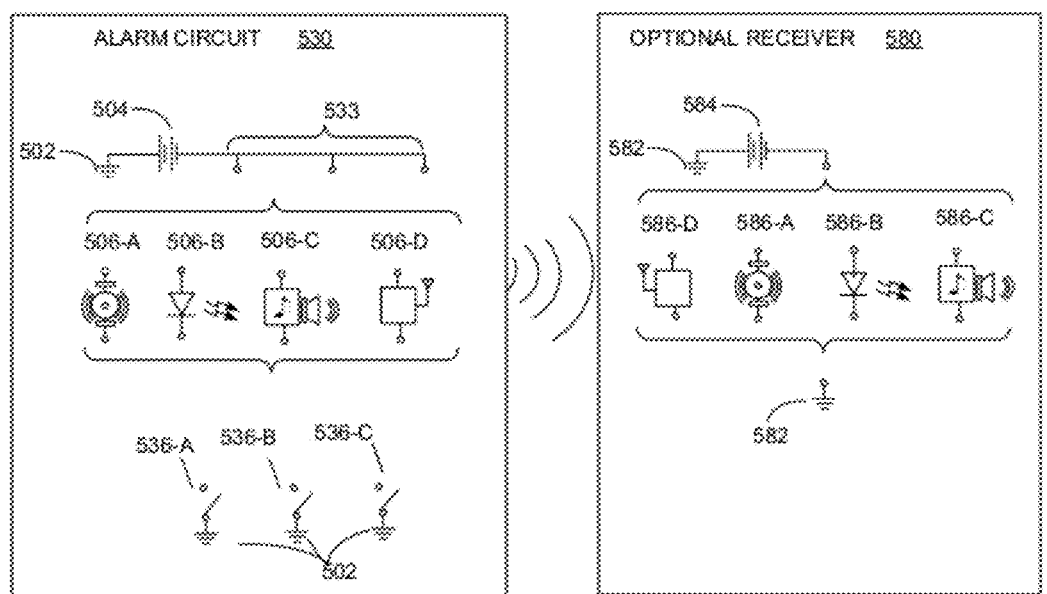
FIG. 5B is a schematic of an alarm circuit and optional receiver circuit, with multiple optional alarm indicators for monitoring conditions of different moisture sensors, according to one or more embodiments.

Referring now to FIG. 5B, a schematic of an alarm circuit 530 and optional receiver circuit 580, each with multiple optional alarm indicators for different conditions from multiple moisture sensors indicating the presence of moisture is shown, according to one or more embodiments. Alarm system 530 comprises: logic indicated in schematic having a normally open moisture sensor circuit; a power source 504, coupled to ground 502 and to the logic; wherein the alarm system 530 may be reusable or disposable; an optional transmitter 506-D that signals to an optional receiver base station 580 when the alarm system is activated; and a plurality of alarm indicators coupled in parallel to one of a plurality of moisture sensors, e.g., 536-A for urine detection, 536-B for feces detection, and 536-C for a duplicate or some other type of detection, where each of the plurality of alarm indicators also coupled to one of multiple contacts 533, which are in turn coupled to battery source 504. Thus, each of the plurality of alarm indicators 506-A thru 506-D can provide a unique alarm indicator for identifying a specific location in the diaper that has moisture, or to indicate a specific type or quantity of fluid or discharge from the user by using material sensitive to the type of fluid, or by using a moisture sensor with a housing tailored to activate based upon a quantity of moisture present. The alarm indicator can be any individual or any combination of alarms shown, e.g., a tactile alarm indicator 506-A, a visual alarm indicator 506-B, an audio alarm indicator 506-C, and a wireless signal alarm indicator 506-D, e.g., having an optional data message output from build in memory. Components are shown as individual components to illustrate the flexibility of combinations that can be coupled together as desired by designer. Plurality of moisture sensors 536-A, 536-B and 536-C in schematic corresponds to a plurality of moisture sensors 301, 302, and 303 disposed in one or more different locations in diaper 200-E shown in FIG. 2E; while tactile, audio, and visual alarm indicator 506-A and/or 506-C and 506-B in schematic correspond to tactile/audio alarm indicator 252 and LED alarm indicator 226, respectively, as shown in section view 200-D of FIG. 2D. Optional receiver 580 includes similar devices and layout as alarm circuit 530, namely power source 584, receiver 586-D, and one or more optional alarms, e.g., vibrating tactile alarm indicator 586-A, light emitting alarm indicator 586-B, audible alarm 586-C with same features as audible alarm 506-C, all of which can be coupled to ground 582.

Figure 5C:
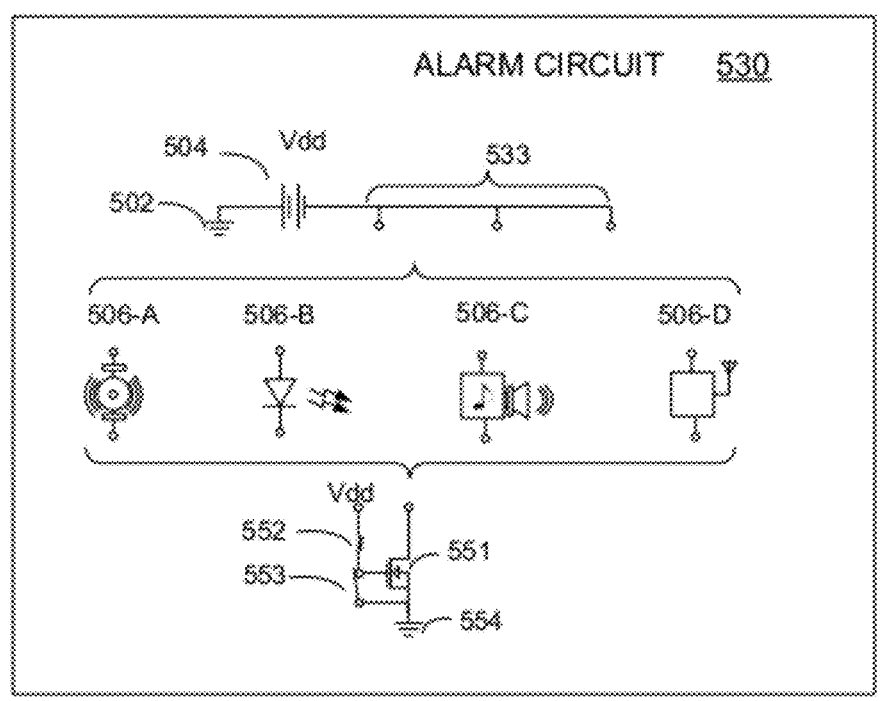
FIG. 5C is a schematic of an alarm circuit with a normally closed switch that activates an alarm when the switch is opened by the presence of moisture, according to one or more embodiments.

Referring now to FIG. 5C, a schematic 530 of an alarm circuit with a normally closed switch 553 that activates an alarm when the switch is opened by the presence of moisture is shown, according to one or more embodiments. Alarm circuit 530 has a power source 504 coupled to ground 502 and coupled via parallel wiring 533 to one or more alarm indicators 506-A through 506-D that are in turn coupled to a single normally closed switch 553. Logic is embodied as a body-biased enhancement-mode NMOS field effect transistor (FET) 551 that does not conduct when the voltage from gate to source, Vgs, is below a threshold voltage. This condition exists when moisture sensor switch 553 is closed and the gate and the source are tied to ground 554, and thus below the threshold voltage. In contrast, NMOS 551 turns on and conducts when its Vgs is above a threshold voltage which condition arises when moisture sensor switch 553 changes to an open state and Vgs falls below the threshold voltage. Thus gate of transistor 551 is no longer tied to conduct to ground but exceeds the threshold voltage as it approaches Vdd. With drain coupled to alarm indicator, e.g., audible alarm indicator 506-C, will now conduct electricity through NMOS 551 to power the alarm indicator. Alternatively, a complementary metal oxide semiconductor can be used in place of body-biased NMOS FET 551.

With above circuits in FIGS. 5A through 5C, once the alarm is activated it remains in an "on" state until moisture sensor is removed, thereby opening the circuit, or by manual reset, or until the moisture sensor is replaced. Alarm can be continuous, or can have a duty cycle circuit that powers the alarm indicator a fraction of time on a cycle.

Figure 6:
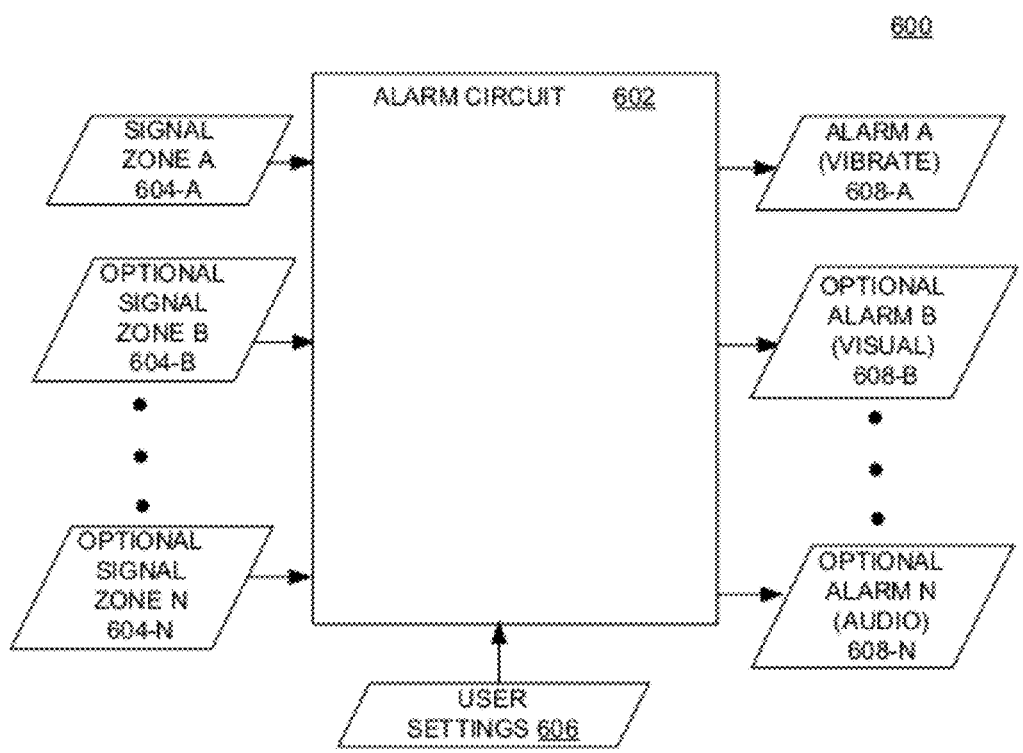
FIG. 6 is a block diagram of the alarm circuit functions for indicating the presence of moisture, according to one or more embodiments.

Referring now to FIG. 6, a block diagram 600 of the alarm circuit functions for indicating the presence of moisture is shown, according to one or more embodiments. Alarm circuit function 602 can receive one or more input signals, e.g., function 604-A from zone A, and optionally input signal function 604-B from zone B through input signal function 604-N from zone N, where N is any quantity desired by the user. User settings input 606 provides for a wide range of functional settings, such as operational test of alarm and power source, optional transmitter and receiver, as well as duration, intensity, frequency, and escalation options for alarm signal, and any other controllable variable for adjusting the alarm signal provided to the user or his care provider. Output functions from alarm circuit function 602 include one or more alarm signals, e.g., alarm A 608-A, a piezo electric vibrating tactile alarm, and optional alarms B 608-B, a visual LED alarm, through audible alarm N 608-N, where N is a desired number of alarms. Signal functions can be implemented for example, by three moisture sensors 301 through 303 as shown in FIG. 2F, wired in series for an "OR" function alarm activation for any of the sensors undergoing a state change, or wired in parallel to unique alarms for segregated individual alarm functions, e.g., moisture sensor 301 coupled to a light emitting diode (LED) alarm output function 608-A, moisture sensor 302 coupled to an audible alarm output 608-B, and moisture sensor 303 coupled to audible alarm output 608-N. Functions of FIG. 6 are illustrated in structures, e.g., alarm 250, and schematics, e.g., 500, 550, 530, and 580, and in procedures, e.g., 800-A, and 800-B, described herein, and their equivalents.

Manufacturing Apparatus

Referring now to FIGS. 7A through 7D, manufacturing system 700-A is shown for fabricating a moisture sensor, according to one or more embodiments. System 700-A includes: a jig base plate 702 with a first retaining wall 707 for supporting a pressure plate 704 that is slidingly coupled thereto via a load actuator 712, e.g., a drive screw or a hydraulic piston; a second retaining wall 706, with an optional split line for access to pressure driver 712; a shaped trough 710, formed into jig base plate 702, with desired shape, e.g., hemicylindrical, for half of the moisture sensor; and top die 730, which also has a portion of the shape desired for the other half of the moisture sensor. Manufacturing system 700-A can be a single unit used to create a length of compressed material that can be cut into individual sensor housings, or can have multiple instances in parallel so as to create multiple instances of moisture sensor housings, e.g., using a pressure driver that extends into adjacent parallel manufacturing system instances. Other support features such as bearings, bushings, drive motors, lubrication, etc. that enable operation of manufacturing system, as known by those skilled in the art. System 700-A can be designed for any size moisture sensor as desired for a given application, e.g., from infant to adult diapers to other industrial moisture sensing applications.

Referring now to FIGS. 7B, 7C, and 7D, sequential stages of the manufacturing system 700-A for fabricating the moisture sensor are shown, according to one or more embodiments. In particular, FIG. 7B illustrates a mandrel 720 having moisture sensitive material 722-A wound or packed around it in an uncompressed state, and disposed in the cavity of the jig base plate 702 between second retaining wall 706 and the pressure plate 704. Mandrel 720 can float laterally and vertically such that it can translate sideways and downward during the subsequent compression stages. Mandrel can be multi-piece apparatus that reduces size for ease in removal from a formed housing. FIG. 7C illustrates the lateral compression of the moisture sensitive material 722-B by pressure plate 704 being actuated in a lateral direction by load actuator 712 to approximately the desired finished width of the moisture sensor housing. FIG. 7D illustrates the vertical compression process of the moisture sensitive material 722-C by top tie 730 which compresses the moisture sensor housing to its final shape, which in the present embodiment is a round cross-section. Forces up to ten to one-hundred tons or more are used to compress the moisture sensitive material 722 into the desired shape to a compressed to a highly-compressed moisture-sensitive material. Alternatively, moisture sensor housing can be fabricated without an internal cavity by either eliminating the use of the mandrel or by removing the mandrel from the process prior to a final compression process. Electrical contacts can be installed within the internal cavity or on the outer surface of the housing, depending on the configuration, e.g., see FIGS. 3A-3D, 3K-3P and 4A-4B, 4D-4F, 4H-4Q, and optionally retained via adhesive, friction fit, crimping, or other fastening means.

Methods

Figure 8A:
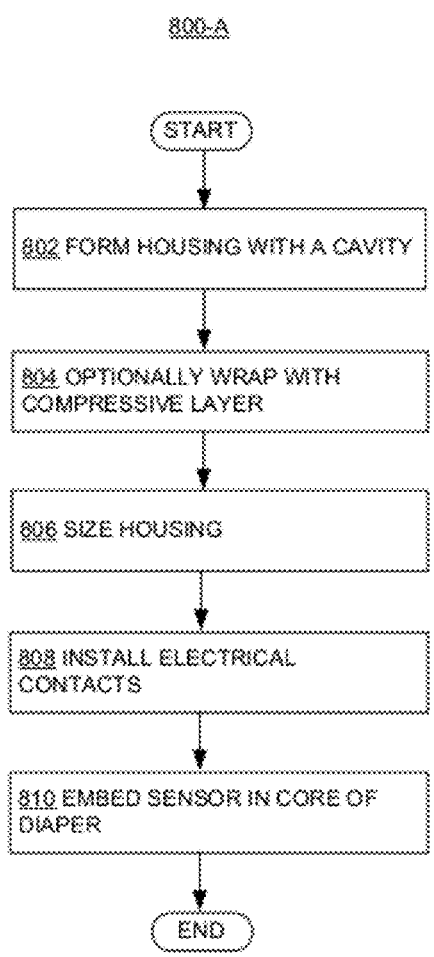
FIGS. 8A and 8B are flow charts of the method to manufacture a moisture sensor and a method for fabricating a diaper with a moisture detection and alarm system for indicating the presence of moisture, according to one or more embodiments.
Figure 8B:
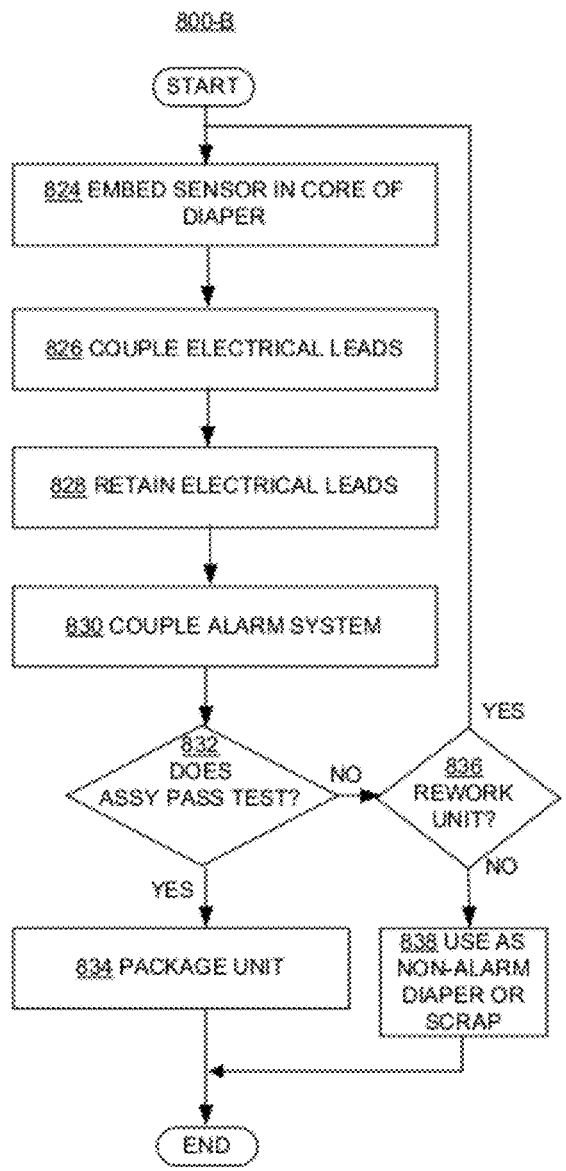

FIGS. 8A and 8B provide flowcharts for processes to manufacture or use the moisture sensor apparatus in the end application, e.g., a diaper, as described and illustrated in FIGS. 1 through 7D. Referring now to FIG. 8A, a flow chart 800-A of the method of fabricating a moisture sensor having a system for detecting the presence of moisture is shown, according to one or more embodiments. The method comprises one or more operations as follows.

In operation 802, a housing is formed with a cavity. Manufacturing system 700-A provides one embodiment of fabricating a moisture sensor housing by winding moisture-sensitive, or moisture-wicking, material around a mandrel, and applying pressure via one or more die or retaining wall to obtain the desired shape and dimension of a raw housing. The compressive nature of forming the sensor housing provides a compact material that is rigid and sufficient to withstand the weight of a user, e.g., infant or adult, without crushing or collapsing. The present disclosure is well-suited to any method of forming housing, such as shaping, pouring, forming, curing, injecting, etc. moisture sensitive material into a mold, press, etc.

Operation 804 optionally wraps moisture sensor housing with a compressive layer moisture-sensitive, or moisture-wicking, material as shown and described in FIGS. 3M through 3P. Wrap may be applied after housing final size is complete, followed by an optional die press to confirm wrap and/or embed wrap into housing. Wrap may be optionally and adhesively bonded at point locations to moisture sensor housing. Compressive sleeve may be applied in one state and processed to place it in another state. For example, a shrink wrap plastic weave, e.g., polyolefin, with venting to allow moisture penetration to housing, may be disposed over housing and heated to cause shrinkage and to create a nominal compressive state in housing that does not cause electrical contacts to contact each other in the absence of moisture. Turning to operation 806, housing is sized by cutting, lasing, or otherwise changing the length of a raw housing to a desired length for a given application, after removing mandrel from raw housing for internal cavity configuration.

Operation 808 installs electrical contacts in or on housing for moisture sensor, depending on the configuration as a normally open or normally closed circuit, as illustrated and described hereinabove. Electrical contacts can be positioned on mandrel prior to, or together with, fabrication of housing, or electrical contacts can be inserted, crimped, adhered to, or otherwise attached on or in housing after housing formation, to provide for stable adherence, to avoid dislodging or accidental contact in a dry environment that would create a false positive of the presence of moisture. Electrical contacts can extend outside of housing, or can include a short lead for subsequent coupling with electrical leads to alarm system. Operation 810 disposes one or more moisture-sensitive sensors in the core of an article application. An exemplary application is a adult or infant diaper, wherein the sensor may be placed, attached or embedded in a wide range of locations, either towards the front and/or back of the diaper, and/or at different depths of the diaper, e.g., between the stay-dry wicking top layer and the absorbent pad layer for an early indicator of moisture, or within the absorbent pad for a nominal indicator of moisture, or behind the absorbent pad, e.g., to indicate soak through condition. Sensor may be retained by stitching, adhesive, inherent fabric integrity, e.g., matted fibers of absorbent pad, or by retention of leads from sensor placed in between layers.

Referring now to FIG. 8B, a flowchart 800-B of a method for fabricating a diaper with a detection and alarm system for indicating the presence of moisture is shown, according to one or more embodiments. Operation 824 disposes one or more moisture-sensitive sensors in the core of an article application, as described in operation 810. Operation 826 couples the sensor, e.g., a first and second contact, with a first and second electrically conductive wire or metal strip lead, wherein the first and second electrically conductive wire or metal strip are insulated or are separated by electrically insulative layers of the diaper. Contacts may be coupled to sensor leads by solder of metallic parts, or by ultrasonic welding, electrically conductive adhesive, crimping, or any other process that creates a robust and electrically conductive connection between metallic and/or electrically conductive polymer components.

Process 828 retains electrical leads in diaper by adhesive backing on strip or wire lead, to retain and separate leads with an insulative distance, e.g., disposing the electrically conductive wire or metal strip to the moisture-proof backing layer, or with a physical barrier, such as a dielectric diaper material.

Process 830 couples sensor via electrical leads to alarm system via a quick release coupling that allows the alarm system to be removed and reused among multiple diapers, so as to reduce the waste from electronics and batteries, thereby leaving a substantially biodegradable diaper and sensor. One of ordinary skill in the art is familiar with the plethora of quick electrical disconnects that will provide a simple, safe, and effective coupling means.

Process 832 performs a built-in self-test to inquire whether the diaper/sensor/alarm/optional transmitter and/or receiver assembly passes a test. Passing the test allows assembly to proceed to operation 834 of packing the unit for sale. Failing the test results in a subsequent operation of deciding whether to rework the unit 836, where a negative response results in the diaper being scrapped, and where positive decisions result in the replacement of sensor(s) and/or alarm and repeat of test.

The Process and method descriptions hereinabove may be performed in a different sequence than the embodiment disclosed, with new processes inserted therein, and/or listed processes optionally altered or removed.

Figure 9A:
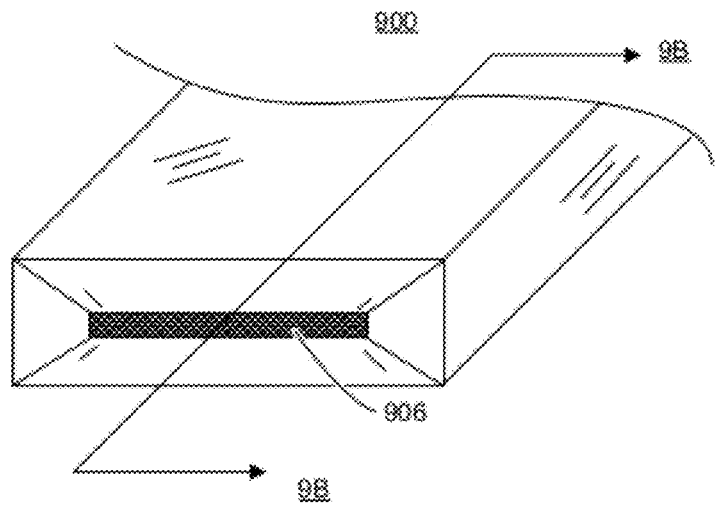
FIGS. 9A and 9B are oblique views of a brush connector system for mating the sensor leads to the alarm system, according to one or more embodiments.
Figure 9B:
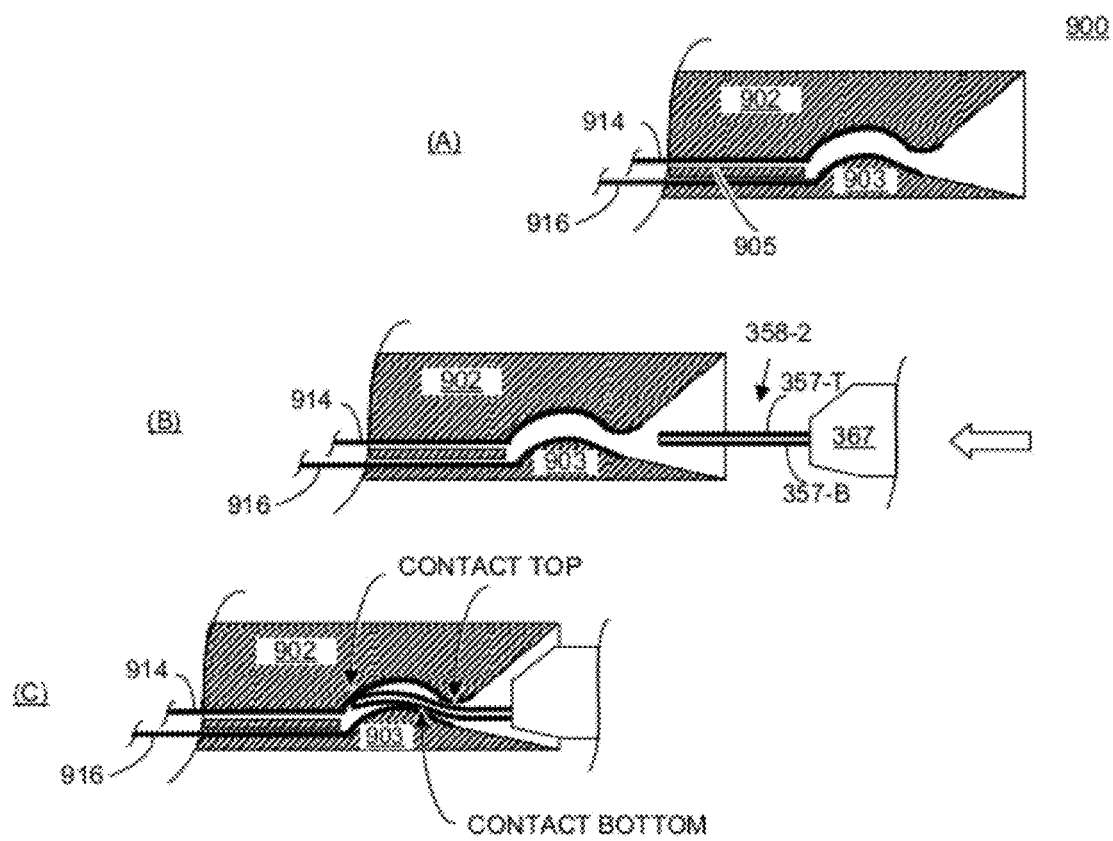

Referring now to FIGS. 9A and 9B, oblique views of a brush connector system 900 for mating the sensor leads to the alarm system is shown, according to one or more embodiments. Connector 900 has a recessed opening 906 with tapered faces to aid in the centering and acceptance of a lead therein. As shown in FIG. 9B view (A), connector 900 has a top portion 902 and bottom portion 903 made of insulative material with connector leads 914 and 916 conformally coupled thereto, e.g., via adhesive or fasteners, to present a smooth and gradually curved path, through which lead 358-2 from sensor can easily navigate. Insulative spacer 905 isolates leads 914 and 916 from each other. With connector lead 914 exposed on top portion of the curved path, and with connector lead 916 exposed on the bottom portion of the curved path inside connector 900, lead 358-2 from sensor, with retainer head 367, automatically makes multiple brush contacts with its top conductive layer 357-T and bottom conductive layer 357-B, as shown in view (C), with both connector leads 914 and 916, respectively, due to the elastic properties of sensor lead 358-2 to remain straight. Lead 358-2 is retained in connector 900 by pocket 221, with hook and loop fastener 221-B coupled to diaper 200-D, as shown in FIG. 2D, to securely retain alarm system 250. This system allows a quick and easy method of inserting and removing two-sided conductive polymer strip 358-2. An alternative embodiment utilizes a pair of single-sided conductive leads, e.g., 358-1, or two metallic leads, that each fit into one of two connector housings, similar to connector 900, but only needing a single connector lead, 914 or 916, disposed in the appropriate location of either of the two connector housings to mate with the conductive portion of the sensor lead.

The present description is applicable to a wide variety of applications and is not limited to any particular type of materials, measurement markings, sizes or geometries of surfaces. Rather, the present description is applicable to a wide variety of materials, measurement markings, geometries, and arrangements that meet the marking functions listed herein.

The foregoing descriptions of specific embodiments of the present disclosure have been presented for purposes of illustration and description. They are not intended to be exhaustive or to limit the invention to the precise forms disclosed. Many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

I claim:

1. A sensor for detecting moisture in an absorbent article, the sensor comprising:
    a housing made of material that is dimensionally-sensitive to a presence of moisture;
    a plurality of electrically conductive contacts disposed on or in the housing;
    wherein the electrically conductive contacts are selectively coupled to, or decoupled from, each other as a result of a dimensional change of the housing arising from exposure to moisture; and
    wherein an electrical signal routable through the selectively coupled electrically conductive contacts creates a closed or an open circuit to indicate the presence of moisture.

2. The sensor of claim 1 wherein the housing has an outer surface and a cavity formed therein, and wherein the plurality of electrically conductive contacts is disposed on an inner wall of the cavity.

3. The sensor of claim 1 wherein:
    the plurality of electrically conductive contacts are initially disposed apart from each other in a substantially dry environment to represent a normally open circuit that does not activate a moisture alarm; or
    the plurality of electrically conductive contacts is initially disposed against each other in the substantially dry environment to represent a normally closed circuit that does not activate the moisture alarm.

4. The sensor of claim 1 wherein the housing is formed into a shape having a cylindrical, oval, or rectangular cross-section.

5. The sensor of claim 2 further comprising:
    an outside layer disposed around the housing, wherein the outside layer helps to maintain a shape of the housing, and wherein the outside layer is a fibrous material disposed on the outer surface of the dimensionally-sensitive material in order to inhibit expansion of the outer surface of the housing and to promote closure of the cavity formed inside the housing.

6. The sensor of claim 1 wherein the dimensionally sensitive material used for the housing is highly compressed.

7. The sensor of claim 1 wherein at least a portion of the sensor is a consumable one-time use device that is at least partially biodegradable.

8. The sensor of claim 1 further comprising:
    a plurality of electrically conductive leads, each of which is respectively coupled to one of the plurality of electrically conductive contacts;
    wherein the electrically conductive contacts or the conductive leads therein are made from an electrically conductive polymer that is either at least partially biodegradable.

9. The sensor of claim 1 wherein the housing with dimensionally sensitive material expands at least 30% in the presence of moisture.

10. A system for detecting moisture, the system comprising:
    a moisture-resistant layer;
    an absorbent material coupled to the moisture-resistant layer;
    a moisture sensor disposed in or on the absorbent material, wherein the sensor has a plurality of electrical contacts coupled thereto, and wherein the sensor detects moisture by changing a state of the plurality of electrical contacts from a normally open to a closed, or from a normally closed to an open position, under the force of mechanical expansion or contraction of the sensor in the presence of moisture;
    a plurality of electrically conductive leads, wherein each of the electrically conductive leads is respectively coupled to one of the plurality of electrically conductive contacts on the moisture sensor; and an alarm system coupled to the electrically conductive leads, wherein the alarm system is activated by the change of the state of the electrical contacts in the moisture sensor.

11. The system of claim 10 further comprising:
a plurality of moisture sensors for detecting moisture coupled to the alarm system, wherein any one of the plurality of moisture sensors can independently activate the alarm system due to detection of moisture.

12. The system of claim 11 wherein at least one of the plurality of moisture sensors, coupled via the electrically conductive leads to a unique alarm indicator, is disposed in a front of the diaper to detect urine.

13. The system of claim 11 wherein at least one of the plurality of moisture sensors, coupled via the electrically conductive leads to a unique alarm indicator, is disposed in the rear of the diaper to detect feces.

14. The system of claim 10 wherein the alarm system is selectively coupled to the electrically conductive leads such that the alarm system can be removed and reused, while the absorbent material and the moisture sensor can be discarded.

15. The system of claim 10 wherein the alarm device further comprises:
an alarm indicator coupled to the logic and the sensor, the alarm indicator producing an audio, visual, tactile, or data output when activated.

16. The system of claim 10 wherein the alarm device further comprises:
a connector having a plurality of brush contacts that selectively couple to the plurality of electrically conductive leads from the moisture sensor.

17. An alarm system for indicating a presence of moisture in an absorbent article, the alarm system comprising:
a sensor for detecting moisture, the sensor having a housing made of material dimensionally sensitive to the presence of moisture;
logic for determining when an electrical circuit coupled to the sensor changes from a normally open position to a closed position or from a normally closed position to an open position; and
a power source coupled to the logic.

18. The alarm system of claim 17 further comprising:
a wireless transmitter coupled to a battery and to a remote alarm indicator wherein the wireless transmitter has a duty cycle less than 50% for transmitting a signal to the remote alarm indicator device having audio, visual, tactile, or data indicating means for an alarm.

19. The alarm system of claim 17 further comprising:
an indicator chosen from a group of:
an operational indicator coupled to the logic and batter for indicating the operational status of the transmitter and the operational status of the battery source; and
an alarm indicator coupled to the logic and the sensor, the alarm indicator producing an audio, visual, tactile, or data output when activated.

20. The alarm system of claim 18 wherein the wireless transmitter can transmit at different frequencies for pairing with a specific alarm of a base receiving station.

* * * * *